US009845458B2

(12) United States Patent
Matsuyama et al.

(10) Patent No.: US 9,845,458 B2
(45) Date of Patent: Dec. 19, 2017

(54) MULTIPOTENT PROGENITOR CELL DERIVED FROM ADIPOSE TISSUE

(75) Inventors: Akifumi Matsuyama, Kobe (JP); Hiroshi Komoda, Chiba (JP); Hanayuki Ohkura, Suita (JP); Yoshiki Sawa, Suita (JP)

(73) Assignee: Akifumi Matsuyama, Hyogo (JP)

( * ) Notice: Subject to any disclaimer, the term of this patent is extended or adjusted under 35 U.S.C. 154(b) by 399 days.

(21) Appl. No.: 12/664,343

(22) PCT Filed: Jun. 16, 2008

(86) PCT No.: PCT/JP2008/060977
§ 371 (c)(1),
(2), (4) Date: Dec. 29, 2009

(87) PCT Pub. No.: WO2008/153179
PCT Pub. Date: Dec. 18, 2008

(65) Prior Publication Data
US 2010/0151574 A1 Jun. 17, 2010

(30) Foreign Application Priority Data

Jun. 14, 2007 (JP) ................. 2007-157387
Jun. 14, 2007 (JP) ................. 2007-157388

(51) Int. Cl.
*C12N 5/00* (2006.01)
*C12N 5/0775* (2010.01)
(52) U.S. Cl.
CPC .................. *C12N 5/0667* (2013.01)
(58) Field of Classification Search
None
See application file for complete search history.

(56) References Cited

U.S. PATENT DOCUMENTS

| 2006/0154235 A1 | 7/2006 | Ochiya et al. |
| 2007/0148766 A1 | 6/2007 | Yoshimura et al. |
| 2010/0322906 A1* | 12/2010 | Matsuyama et al. ........ 424/93.7 |

FOREIGN PATENT DOCUMENTS

| EP | 1842905 A1 | 10/2007 |
| JP | 2002537849 A | 11/2002 |
| JP | 2005502352 A | 1/2005 |
| WO | 00/53795 A1 | 9/2000 |
| WO | 03022988 A2 | 3/2003 |
| WO | 03039489 A2 | 5/2003 |
| WO | WO 2005042730 * | 5/2005 |
| WO | 2006134951 A1 | 12/2006 |
| WO | 2007039986 A1 | 4/2007 |

OTHER PUBLICATIONS

Shi et al. (Hepatology Research, 2005, vol. 31, pp. 223-231).*
Miki et al (Cell Transplant, 2006. vol. 15, No. 4, pp. 325-334).*
Hassan Afizah, et al.;"A Comparison Between the Chondrogenic Potential of Human Bone Marrow Stem Cells (BMSCs) and Adipose-Derived Stem Cells (ADSCs) Taken from the Same Donors" ; Tissue Engineering; vol. 13, No. 4, pp. 659-666 (2007); Mary Ann Liebert, Inc. (Cited in the counterpart int'l search report).
Margarita de la Llera, et al. ;"Mechanism of triglyceride accumulation in rat preadipocyte cultures exposed to very low density lipoprotein"; Journal of Lipid Research; vol. 22, pp. 245-253 (1981); ASBMB. (Cited in the specification).
John K Fraser et al.;"Fat tissue:an underappreciated source of stem cells for biotechnology"; TRENDS in Biotechnology; vol. 24; No. 4, pp. 150-154 (Apr. 2006); Science Direct. (Cited in the counterpart European search report).
Agnieszka Banas et al.;"Human adipose tissue-derived stem cells as a source of functional hepatocytes";65th Proceedings of the Japanese Cancer Association;vol. 65, pp. 504-505 (Aug. 28, 2006).
Takahiro Ochiai ;"Reasearch on usage of live cells differentiation-induced from stem cells "; Heisei 17 Nendo Soyakuto Human Sience Kenkyu Buntan Kenkyu Hokokusho;pp. 45-49(2006) (English translation for boxed text is attached.).
Agnieszka Banas, et al.;"Human adipose tissue-derived stem cells as a source of functional hepatocytes"; Regenerative Medicine; vol. 6, pp. 260 (2007); ICLS.
JM Gimble et al.;"Adipose-derived adult stem cells: isolation, characterization, and differentiation potential"; Cytotherapy; vol. 5, No. 5, pp. 362-369(2003);ISCT.
Min Jeong Seo et al.;"Differentiation of human adipose stomal cells into hepatic lineage in vitro and in vivo"; Biochemical and Biophysical Research Communications 328; pp. 258-264 (2005).
Li, S. et al.;"Differentiation of human adipose derived mesenchymal stem cells into hepatocyte-like cells in vitro"; Tissue Engineering;vol. 12, No. 4, p. 1111 (2006).
Guilak, F. et al.;"Adipose-derived adult stem cells for cartilage tissue engineering"; Biorheology;vol. 41, pp. 389-399 (2004).
Schaeffer, A. et al.;"Concise review: adipose tissue-derived stromal cells—basic and clinical implications for novel cell based therapies"; Stem Cells;vol. 25, No. 4, pp. 818-827(2007).
Zuk, P.A. et al.;"Human adipose tissue is a source of multipotent stem cells"; molecular Biology of the cell;vol. 13, No. 12, pp. 4279-4295 (2002).
Imamura, T. et al.;"Embryonic stem cell-derived embryoid bodies in three-dimensional culture system form hepatocyte-like cells in vitro and in vivo"; Tissue Engineering;vol. 10, pp. 1716-1724 (2004).

(Continued)

*Primary Examiner* — Celine X Qian
(74) *Attorney, Agent, or Firm* — MetroLexis Law Group, PLLC

(57) ABSTRACT

Disclosed is a cell mass containing an adipose-tissue-derived multipotent progenitor cell. Also disclosed is a method for producing an adipose-tissue-derived multipotent progenitor cell from an adipose tissue, which comprises the steps of: (a) removing erythrocytes from an adipose-tissue-derived cell mass to produce a preadipose-tissue-derived multipotent progenitor cell mass; and (b) removing cells other than the adipose-tissue-derived multipotent progenitor cell from the preadipose-tissue-derived multipotent progenitor cell mass to produce the desired adipose-tissue-derived multipotent progenitor cell. Further disclosed is an adipose-tissue-derived multipotent progenitor cell produced by the method.

7 Claims, 26 Drawing Sheets

(56) References Cited

OTHER PUBLICATIONS

The English translation of the International Preliminary Report on Patentability (Chapter I of the Patent Cooperation Treaty) issued in corresponding international application No. JP2008/060977 dated Dec. 17, 2009, including Forms PCT/IB/373, PCT/ISA/237, PCT/ISA/237, PCT/ISA/237.
The Extended European Search Report issued in corresponding European patent application No. 08765660.9 dated May 21, 2010.
An official action dated Nov. 13, 2012 in a counterpart Japanese patent application.

* cited by examiner

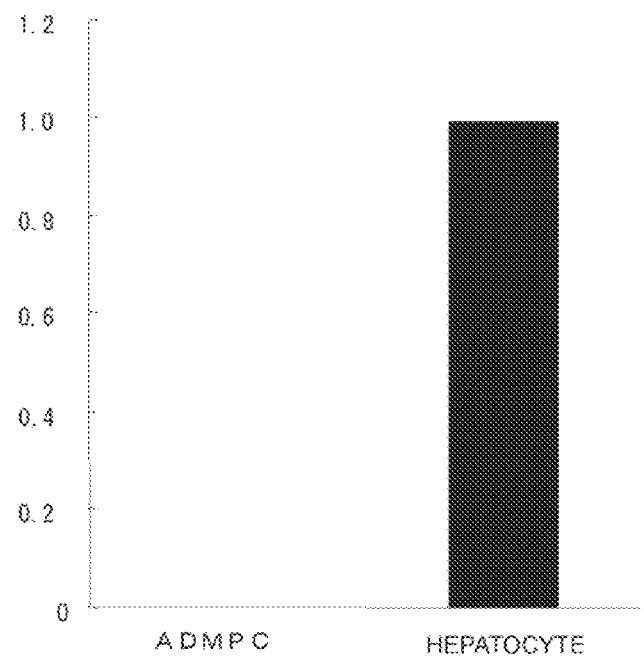
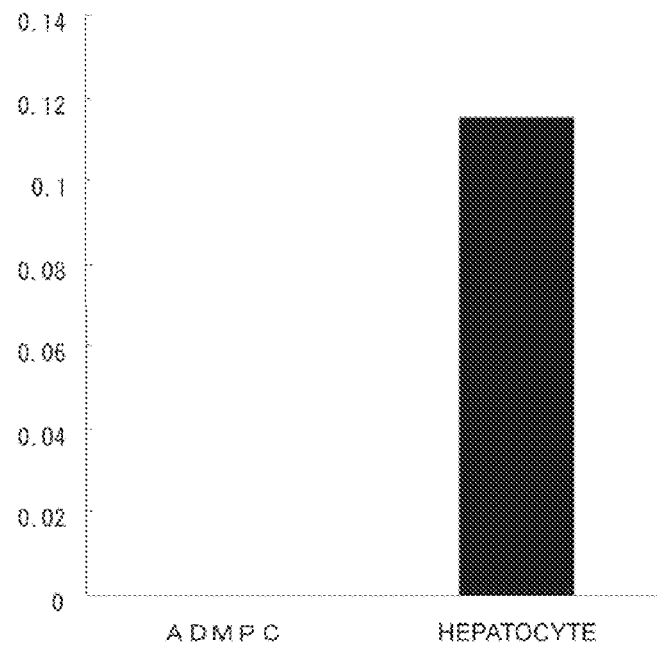

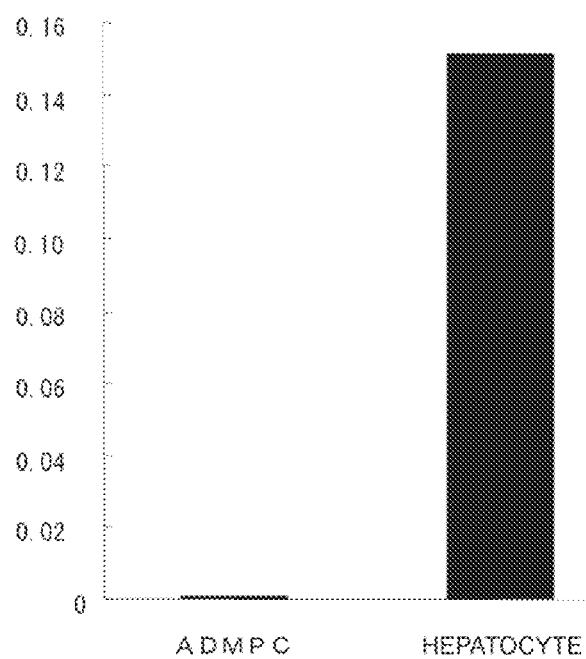
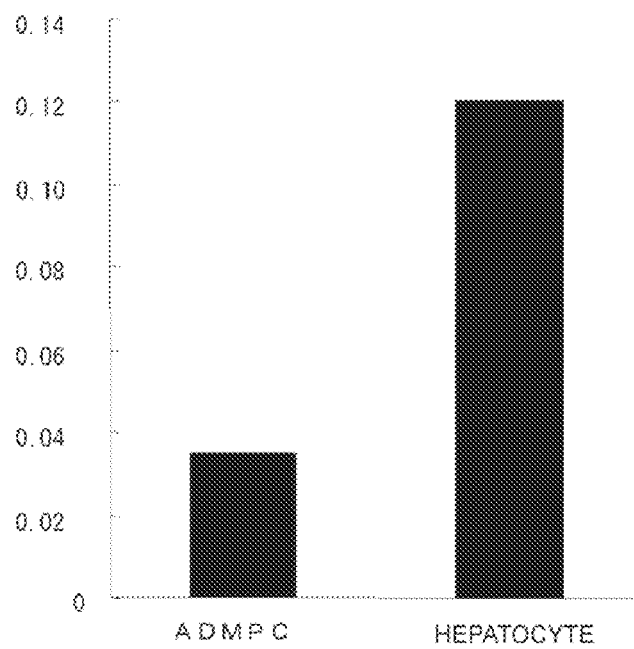

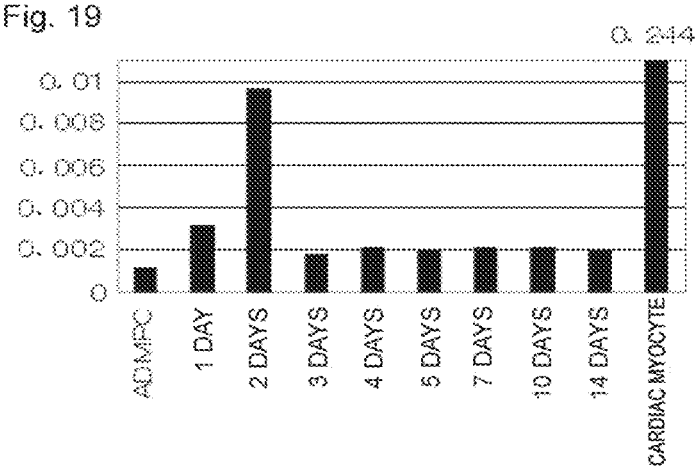
Fig. 19
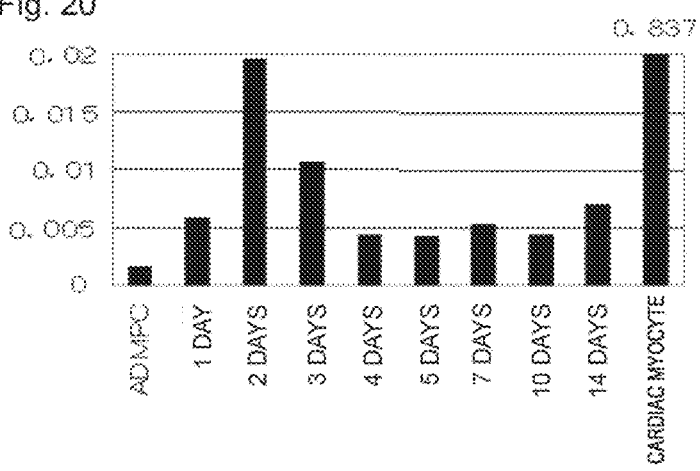
Fig. 20
Fig. 21
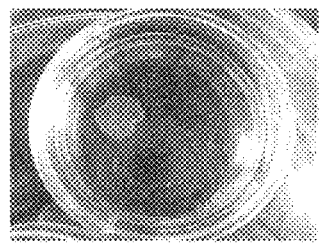

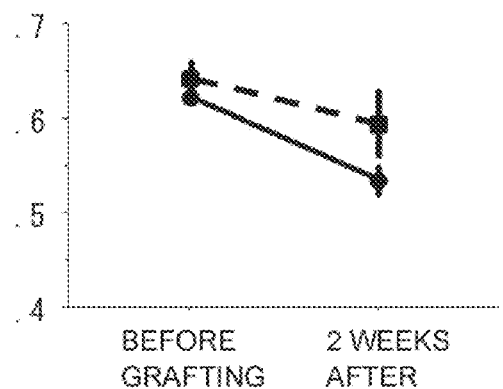
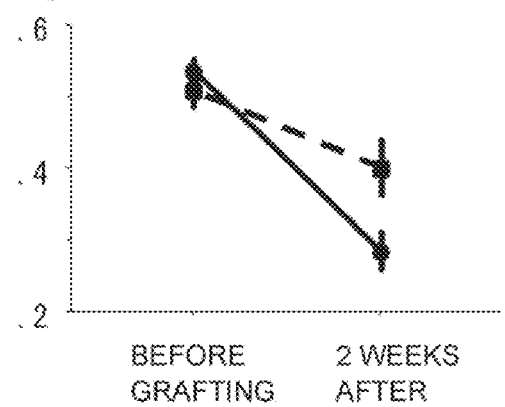
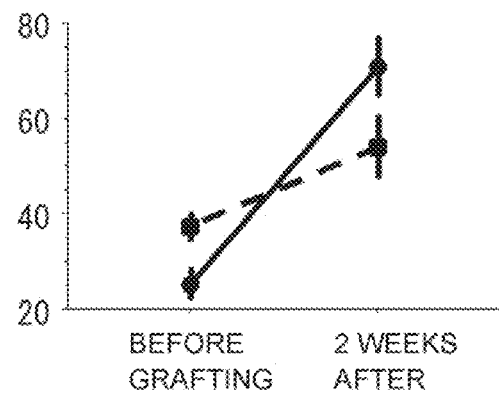

Fig. 39
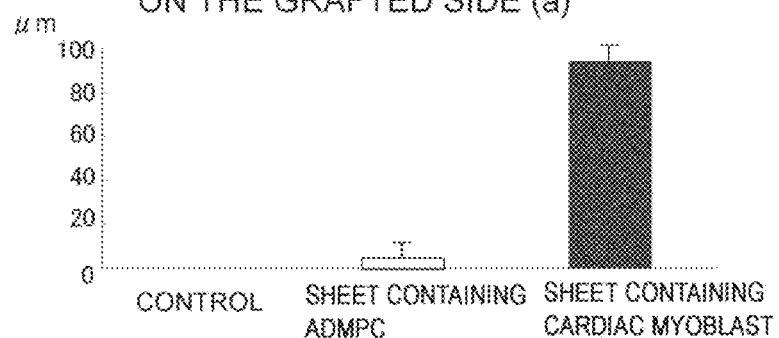
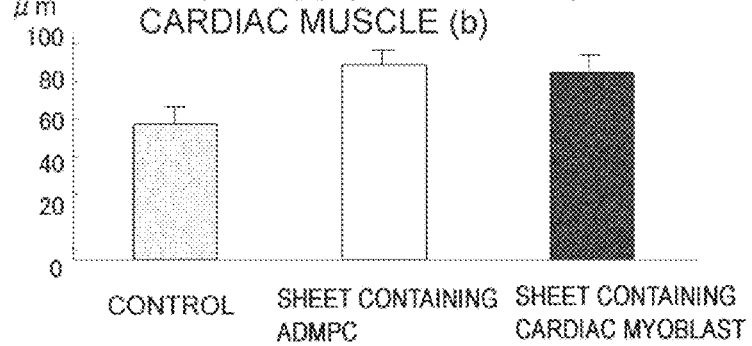
Fig. 40

Fig. 41
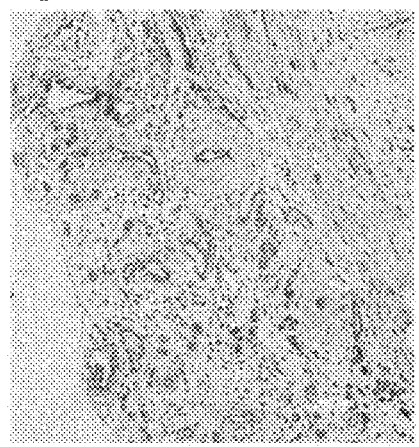
Fig. 42
| ADMPC | ADSC |
|---|---|
| 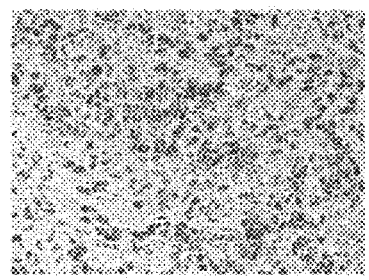 | 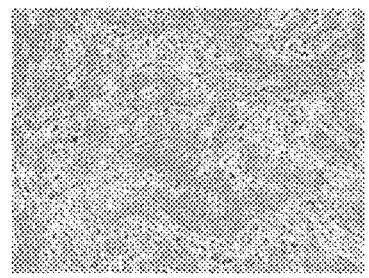 |

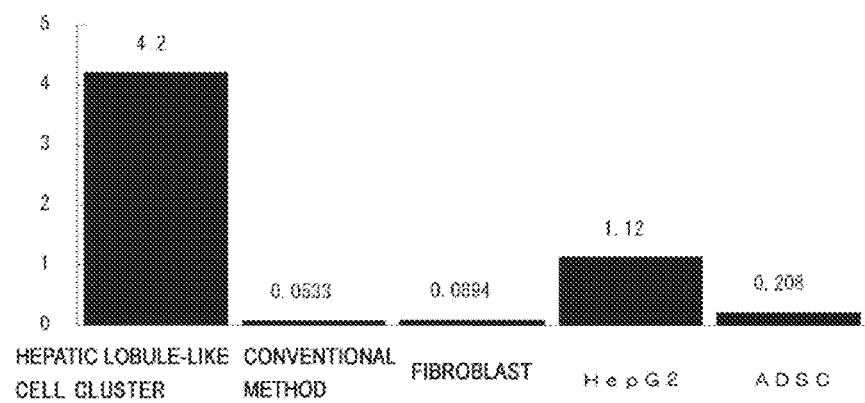
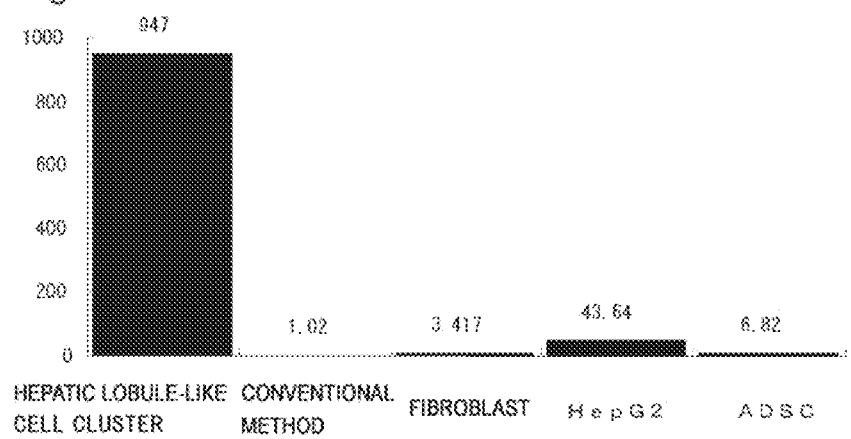
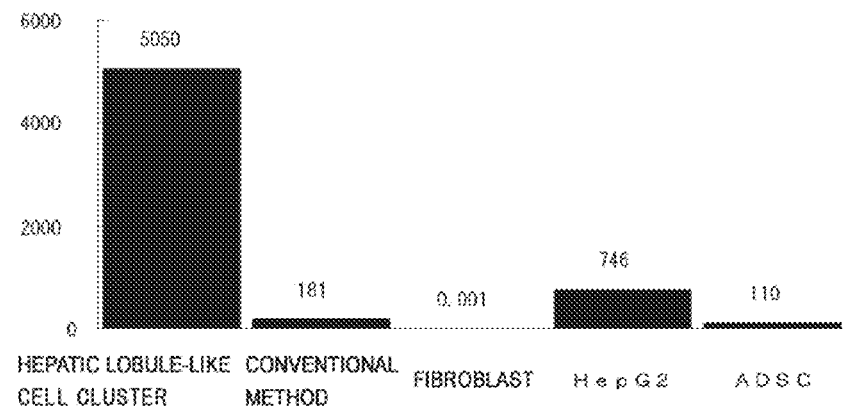

```
                          SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Islet-1 forward primer

<400> SEQUENCE: 1
gtcagtggtg gacctgacct                                                 20

<210> SEQ ID NO 2
<211> LENGTH: 20
<212> TYPE: DNA
<213> ORGANISM: Artificial Sequence
<220> FEATURE:
<223> OTHER INFORMATION: Islet-1 reverse primer
```

<400> SEQUENCE: 2 agggagatt cagtgtggtg                                                    20

<210> SEQ ID NO 3
<211> LENGTH: 21
<212> TYPE: DNA
<213> ORGANISM: Artificial Sequence
<220> FEATURE:
<223> OTHER INFORMATION: Nkx2.5 forward primer

<400> SEQUENCE: 3
ggtggagctg gagaagacag a                                                 21

<210> SEQ ID NO 4
<211> LENGTH: 21
<212> TYPE: DNA
<213> ORGANISM: Artificial Sequence
<220> FEATURE:
<223> OTHER INFORMATION: Nkx2.5 reverse primer

<400> SEQUENCE: 4
cgacgccgaa gttcacgaag t                                                 21

<210> SEQ ID NO 5
<211> LENGTH: 20
<212> TYPE: DNA
<213> ORGANISM: Artificial Sequence
<220> FEATURE:
<223> OTHER INFORMATION: GATA-4 forward primer

<400> SEQUENCE: 5
accagcagca gcgaggagat                                                   20

<210> SEQ ID NO 6
<211> LENGTH: 20
<212> TYPE: DNA
<213> ORGANISM: Artificial Sequence
<220> FEATURE:
<223> OTHER INFORMATION: GATA-4 reverse primer

<400> SEQUENCE: 6
gagagatgca gtgtgctcgt                                                   20

<210> SEQ ID NO 7
<211> LENGTH: 22
<212> TYPE: DNA
<213> ORGANISM: Artificial Sequence
<220> FEATURE:
<223> OTHER INFORMATION: ??-CA forward primer

<400> SEQUENCE: 7
ggagttatgg tgggtatggg tc                                                22

<210> SEQ ID NO 8
<211> LENGTH: 22
<212> TYPE: DNA
<213> ORGANISM: Artificial Sequence
<220> FEATURE:
<223> OTHER INFORMATION: ??-CA reverse primer

<400> SEQUENCE: 8
agtggtgaca aaggagtagc ca                                                22

<210> SEQ ID NO 9

```
<211> LENGTH: 21
<212> TYPE: DNA
<213> ORGANISM: Artificial Sequence
<220> FEATURE:
<223> OTHER INFORMATION: MLC-2v forward primer

<400> SEQUENCE: 9
gcgccaactc caacgtgttc t                                                   21

<210> SEQ ID NO 10
<211> LENGTH: 21
<212> TYPE: DNA
<213> ORGANISM: Artificial Sequence
<220> FEATURE:
<223> OTHER INFORMATION: MLC-2v reverse primer

<400> SEQUENCE: 10
gtgatgatgt gcaccaggtt c                                                   21

<210> SEQ ID NO 11
<211> LENGTH: 20
<212> TYPE: DNA
<213> ORGANISM: Artificial Sequence
<220> FEATURE:
<223> OTHER INFORMATION: MHC forward primer

<400> SEQUENCE: 11
ggggacagtg gtaaaagcaa                                                     20

<210> SEQ ID NO 12
<211> LENGTH: 20
<212> TYPE: DNA
<213> ORGANISM: Artificial Sequence
<220> FEATURE:
<223> OTHER INFORMATION: MHC reverse primer

<400> SEQUENCE: 12
tccctgcgtt ccactatctt                                                     20

<210> SEQ ID NO 13
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 13
gtcagtggtg gacctgacct                                                     20

<210> SEQ ID NO 14
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 14
aggggagatt cagtgtggtg                                                     20

<210> SEQ ID NO 15
<211> LENGTH: 19
<212> TYPE: DNA
<213> ORGANISM: Artificial Sequence
<220> FEATURE:
<223> OTHER INFORMATION: nestin forward primer

<400> SEQUENCE: 15
```

```
ggcgcacctc aagatgtcc                                              19
```

<210> SEQ ID NO 16
<211> LENGTH: 19
<212> TYPE: DNA
<213> ORGANISM: Artificial Sequence
<220> FEATURE:
<223> OTHER INFORMATION: nestin reverse primer

<400> SEQUENCE: 16

```
cttggggtcc tgaaagctg                                              19
```

<210> SEQ ID NO 17
<211> LENGTH: 22
<212> TYPE: DNA
<213> ORGANISM: Artificial Sequence
<220> FEATURE:
<223> OTHER INFORMATION: Neurofilament 68 forward primer

<400> SEQUENCE: 17

```
atgagttcct tcagctacga gc                                          22
```

<210> SEQ ID NO 18
<211> LENGTH: 20
<212> TYPE: DNA
<213> ORGANISM: Artificial Sequence
<220> FEATURE:
<223> OTHER INFORMATION: Neurofilament 68 reverse primer

<400> SEQUENCE: 18

```
gggcatcaac gatccagagc                                             20
```

<210> SEQ ID NO 19
<211> LENGTH: 19
<212> TYPE: DNA
<213> ORGANISM: Artificial Sequence
<220> FEATURE:
<223> OTHER INFORMATION: somatostatin forward primer

<400> SEQUENCE: 19

```
gctgctgtct gaacccaac                                              19
```

<210> SEQ ID NO 20
<211> LENGTH: 19
<212> TYPE: DNA
<213> ORGANISM: Artificial Sequence
<220> FEATURE:
<223> OTHER INFORMATION: somatostatin reverse primer

<400> SEQUENCE: 20

```
cgttctcggg gtgccatag                                              19
```

<210> SEQ ID NO 21
<211> LENGTH: 22
<212> TYPE: DNA
<213> ORGANISM: Artificial Sequence
<220> FEATURE:
<223> OTHER INFORMATION: snail forward primer

<400> SEQUENCE: 21

```
aatcggaagc ctaactacag cg                                          22
```

<210> SEQ ID NO 22
<211> LENGTH: 20
<212> TYPE: DNA

```
<213> ORGANISM: Artificial Sequence
<220> FEATURE:
<223> OTHER INFORMATION: snail reverse primer

<400> SEQUENCE: 22
gtcccagatg agcattggca                                                    20

<210> SEQ ID NO 23
<211> LENGTH: 21
<212> TYPE: DNA
<213> ORGANISM: Artificial Sequence
<220> FEATURE:
<223> OTHER INFORMATION: slug forward primer

<400> SEQUENCE: 23
aagcatttca acgcctccaa a                                                  21

<210> SEQ ID NO 24
<211> LENGTH: 23
<212> TYPE: DNA
<213> ORGANISM: Artificial Sequence
<220> FEATURE:
<223> OTHER INFORMATION: slug reverse primer

<400> SEQUENCE: 24
aggatctctg gttgtggtat gac                                                23
```

MULTIPOTENT PROGENITOR CELL DERIVED FROM ADIPOSE TISSUE

TECHNICAL FIELD

The present invention relates to a cell population that contains an adipose tissue-derived multipotent progenitor cell (hereafter may be referred to as "ADMPC"), a method for obtaining an adipose tissue-derived multipotent progenitor cell from an adipose tissue and to an adipose tissue-derived multipotent progenitor cell obtainable by such a method, and the like.

BACKGROUND ART

In recent years, a path to overcoming intractable diseases has been shown by regenerative medicine and regenerative medical therapies that exploit cell tissue engineering/genetic engineering and the like. Mesenchymal tissue-derived adult stem cells, in particular adipose tissue-derived somatic stem cells, which may be collected safely and simply, have been drawing attention as supply sources of cellular materials used in these regenerative medical therapies.

Adipose tissue-derived somatic stem cells may be collected from an adipose tissue by methods that have been already established in the 1980's (Non-patent Reference 1, and Patent References 1 and 2). However, the collection efficiency of such methods is low, with a large number of erythrocytes and vascular endothelial cells contaminating the cell population obtained ultimately. Since the growth efficiency of the contaminating erythrocytes and vascular endothelial cells is higher than that of stem cells, the proportion of stem cells in the cell population decreases when the obtained cell population is cultured. In addition, when the obtained cell population is induced for differentiation, the differentiation efficiency thereof is remarkably low. Consequently, in order to achieve an actual application clinically or in drug screening and the like, development of a method for collecting adipose tissue-derived somatic stem cells with high purity and high yield is needed.

Patent Reference 1: Japanese Translation of PCT Application No. 2002-537849
Patent Reference 2: Japanese Translation of PCT Application No. 2005-502352
Non-patent Reference 1: de la Llera M et al., J. Lipid Res. 1981 February; 22(2): 245-53

DISCLOSURE OF THE INVENTION

An object of the present invention is to provide a cell population containing an adipose tissue-derived multipotent progenitor cell with a low proportion of undesirable cells other than the adipose tissue-derived multipotent progenitor cell. Furthermore, an object of the present invention is to provide a method for obtaining an adipose tissue-derived multipotent progenitor cell from an adipose tissue and adipose tissue-derived multipotent progenitor cell obtainable thereby, and the like.

The present inventors conducted earnest studies in view of the aforementioned issues, and as a result, discovered that, by removing the erythrocytes and adherent cells such as vascular endothelial cells contained in the adipose tissue respectively by the density method and EDTA, the proportion of the contaminants, that is to say, of cells other than the adipose tissue-derived multipotent progenitor cell, was decreased and the purity and yield of the obtained adipose tissue-derived multipotent progenitor cell increased, and reached completion of the present invention.

That is to say, the present invention provides
(1) a cell population containing an adipose tissue-derived multipotent progenitor cell,
(2) the cell population according to (1), in which the adipose tissue-derived multipotent progenitor cell is one that expresses Islet-1,
(3) a method for obtaining an adipose tissue-derived multipotent progenitor cell from an adipose tissue, comprising the steps of:
(a) removing erythrocytes from an adipose tissue-derived cell population and producing a preadipose tissue-derived multipotent progenitor cell population; and
(b) removing cells other than an adipose tissue-derived multipotent progenitor cell from the preadipose tissue-derived multipotent progenitor cell population and obtaining an adipose tissue-derived multipotent progenitor cell,
(4) the method according to (3), in which the removal of erythrocytes from the adipose tissue-derived cell population is performed by a density method, a hemolysis method or a filtration method,
(5) the method according to (4), in which the removal of erythrocytes from the adipose tissue-derived cell population is performed by the density method,
(6) the method according to any of (3) to (5), in which the removal of cells other than adipose tissue-derived multipotent progenitor cell from the preadipose tissue-derived multipotent progenitor cell population is carried out by a substance other than trypsin,
(7) the method according to (6), in which the substance other than trypsin is a chelator,
(8) the method according to (7), in which the chelator is EDTA,
(9) the method according to any of (3) to (8), in which the cells other than the adipose tissue-derived multipotent progenitor cell are vascular endothelial cells,
(10) an adipose tissue-derived multipotent progenitor cell obtainable by the method according to any of (3) to (9).

The present invention provides a method for obtaining an adipose tissue-derived multipotent progenitor cell from a cell population or an adipose tissue containing an adipose tissue-derived multipotent progenitor cell and an adipose tissue-derived multipotent progenitor cell or the like, obtainable thereby.

BRIEF DESCRIPTION OF THE DRAWINGS

FIG. 11 is a graph showing the amount of expression by quantitative PCR of α-fetoprotein in hepatocytes obtained by causing ADMPC to differentiate. The vertical axis represents AFP (α-fetoprotein)/GAPDH.

FIG. 12 is a graph showing the amount of expression by quantitative PCR of albumin in hepatocytes obtained by causing ADMPC to differentiate. The vertical axis represents albumin/GAPDH.

FIG. 13 is a graph showing the amount of expression by quantitative PCR of CYP1B1 in hepatocytes obtained by causing ADMPC to differentiate. The vertical axis represents CYP1B1/GAPDH.

FIG. 14 is a graph showing the amount of expression by quantitative PCR of glutamine synthase in hepatocytes obtained by causing ADMPC to differentiate. The vertical axis represents glutamine synthase/GAPDH.

FIG. 19 is a graph showing the expression by quantitative PCR of MLC in cells cultured in the presence of DMSO. The vertical axis represents MLC/GAPDH.

FIG. 20 is a graph showing the expression by quantitative PCR of MHC in cells cultured in the presence of DMSO. The vertical axis represents MHC/GAPDH.

FIG. 21 is a strong magnification image of a sheet containing ADMPC-derived cardiac myoblasts.

FIG. 24 is a graph (unit of the vertical axis: mm) showing improvement of LVDd of a heart grafted with a sheet containing ADMPC-derived cardiac myoblasts (circle) and a sheet containing ADMPC (square).

FIG. 25 is a graph (unit of the vertical axis: mm) showing improvement of LVDs of a heart grafted with a sheet containing ADMPC-derived cardiac myoblasts (circle) and a sheet containing ADMPC (square).

FIG. 26 is a graph showing improvement of % EF of a heart grafted with a sheet containing ADMPC-derived cardiac myoblasts (circle) and a sheet containing ADMPC (square).

FIG. 39 is a figure graphed with the thickness of anti-human α-CA antibody-positive regions after grafting sheets containing ADMPC-derived cardiac myoblast and ADMPC as the index.

FIG. 40 is a micrograph (100×) of a heart grafted with a sheet containing cardiac myoblast when immunostained with an anti-human HLA-ABC antibody.

FIG. 41 is a micrograph (100×) of a heart grafted with a sheet containing ADMPC when immunostained with an anti-human HLA-ABC antibody.

FIG. 42 is a figure comparing the states of differentiation into adipocytes for ADMPC and ADSC by oil red O staining.

FIG. 51 is a graph showing the results of quantitative RT-PCR for keratin 18. The vertical axis represents the ratio of the expression of keratin 18 with respect to the expression of GAPDH.

FIG. 52 is a graph showing the results of quantitative RT-PCR for keratin 19. The vertical axis represents the ratio of the expression of keratin 19 with respect to the expression of GAPDH.

FIG. 53 is a graph showing the results of quantitative RT-PCR for CYP1B1. The vertical axis represents the ratio of the expression of CYP1B1 with respect to the expression of GAPDH.

BEST MODE FOR CARRYING OUT THE INVENTION

Figure 1:
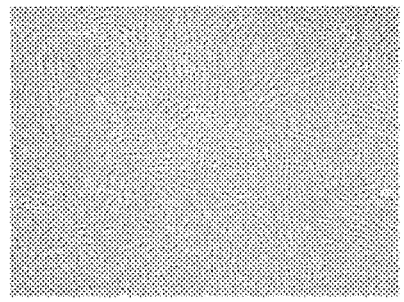
FIG. 1 is a micrograph of ADMPC obtained from an adipose tissue.

In one aspect, the present invention relates to a cell population containing an adipose tissue-derived multipotent progenitor cell. Adipose tissue-derived multipotent progenitor cell refers to a cell, which is a cell that can differentiate into a variety of cell lines such as of the endoderm, mesoderm and ectoderm, and expressing Islet-1, a marker for the absence of differentiation. An adipose tissue-derived multipotent progenitor cell can be obtained from an embryonic stem cell or the like by causing differentiation, in addition to an adipose tissue. The animal species from which the adipose tissue-derived multipotent progenitor cell is derived are not limited in particular, and are preferably, for instance, mammals including human, mouse, rat, rabbit, dog, cat, cow, horse, monkey and the like, and more preferably human. Or, the species similar to or identical to a subject to be treated by a regenerative medical therapy using such a cell population is desirable.

Since the cell population of the present invention has a low proportion of undesired contaminants, for instance, cells other than the adipose tissue-derived multipotent progenitor cell, such as erythrocytes and vascular endothelial cells, it has advantages such as ease of culture and high differentiation efficiency. As measures to eliminate such contaminants, means/methods using the difference with the specific gravity adipose tissue-derived multipotent progenitor cell, for instance, the density method, means/methods using the difference with the adhesiveness of the adipose tissue-derived multipotent progenitor cell, methods using for instance a chelator such as EDTA or an enzyme such as trypsin, antigen-antibody method such as sorting and MACS, methods that select based on morphology, single cell cloning, hemolysis method, and the like, may be cited. The decrease in contaminants within the cell population may be verified, for instance, by quantifying a marker that the contaminant has using methods such as RT-PCR and ELISA, visually under a microscope, or by flow cytometry or immunohistological staining.

The cell population of the present invention preferably contains at least 20%, 30%, 40%, 50%, 60%, 70%, 75%, 80%, 85%, 90%, 93%, 96% or 99% adipose tissue-derived multipotent progenitor cell. Inclusion of adipose tissue-derived multipotent progenitor cells in such proportions gives the cell population of the present invention advantages such as ease of maintenance of the adipose tissue-derived multipotent progenitor cells and high efficiency when [they are] caused to differentiate. In addition to the adipose tissue-derived multipotent progenitor cells, the cell population of the present invention may contain cells that are effective for the maintenance or differentiation of the adipose tissue-derived multipotent progenitor cells, such as, feeder cells, vascular endothelial cells, fibroblasts and the like. Inclusion of such cells may enhance the above advantages.

In another aspect, the present invention relates to a method, which is a method for obtaining an adipose tissue-derived multipotent progenitor cell from an adipose tissue, comprising the steps of (a) removing erythrocytes from an adipose tissue-derived cell population to obtain a preadipose tissue-derived multipotent progenitor cell population, and next, (b) removing cells other than an adipose tissue-derived multipotent progenitor cell from the preadipose tissue-derived multipotent progenitor cell population to obtain an adipose tissue-derived multipotent progenitor cell. The present invention allows adipose tissue-derived cells other than the adipose tissue-derived multipotent progenitor cells to be decreased, and the adipose tissue-derived multipotent progenitor cells to be obtained at high yield and high purity. In the present invention, the above steps may be carried out one after the other, or may be carried out in parallel. The adipose tissue used in this aspect of the present invention may be either of a subcutaneous adipose tissue and a visceral adipose tissue from an organism. The animal species from which the adipose tissue is derived are not limited in particular, and are preferably, for instance, mammals including human, mouse, rat, rabbit, dog, cat, cow, horse, monkey and the like, and more preferably human. Or, the species similar to or identical to the subject to be treated by a regenerative medical therapy using the adipose tissue-derived multipotent progenitor cell obtainable by the method of the present invention is desirable.

The adipose tissue-derived cell population used herein refers to a cell population containing at least an adipose tissue-derived multipotent progenitor cell. The adipose tissue-derived cell population may contain, in addition to an adipose tissue-derived multipotent progenitor cell, erythrocytes, vascular endothelial cells, fibroblasts and the like. The adipose tissue-derived cell population is obtained by treating an adipose tissue, for instance, with an enzyme such as collagenase, or by physical means/method, and/or eliminating lipids and the like, for instance, by centrifugal separation and filtration.

Erythrocytes have the properties of adsorbing adipose tissue-derived multipotent progenitor cells, whereby the yield of adipose tissue-derived multipotent progenitor cell may be decreased. Consequently, it is necessary to eliminate erythrocytes from the adipose tissue-derived cell population. Elimination of erythrocytes from the adipose tissue-derived cell population may be carried out by any means/method, for instance, it may be one carried out by a means/method other than one based on the difference in adhesiveness between the erythrocytes and cells other than these. Preferably, such elimination is carried out by the density method, the hemolysis method or the filtration method, and more preferably, by the density method. The density method may be carried out using a density solution with an adequate density, for instance, a commercially available density solution such as Lymphoprep. It suffices that the density of the density solution used is one between the densities of erythrocytes and cells other than these, preferably 1.063 to 1.119, more preferably 1.070 to 1.110 and most preferably 1.077.

The preadipose tissue-derived multipotent progenitor cell population used herein refers to a cell population containing at least an adipose tissue-derived multipotent progenitor cell. The preadipose tissue-derived multipotent progenitor cell population may contain, in addition to the adipose tissue-derived multipotent progenitor cell, vascular endothelial cells, fibroblasts and the like. As mentioned above, the preadipose tissue-derived multipotent progenitor cell population, in substance, does not contain erythrocytes. By eliminating the erythrocytes to produce a preadipose tissue-derived multipotent progenitor cell population, the subsequent elimination of cells other than the adipose tissue-derived multipotent progenitor cell may be carried out readily and efficiently.

The cells other than the adipose tissue-derived multipotent progenitor cell used herein refer to adherent cells, or the like, such as vascular endothelial cells and fibroblasts. Although elimination of cells other than the adipose tissue-derived multipotent progenitor cells from the preadipose tissue-derived multipotent progenitor cell population may be carried out by any means/methods, it is carried out using preferably a substance other than trypsin, more preferably a chelator such as EDTA or EGTA and most preferably EDTA. Preferably, such elimination is one that is carried out based on the difference in adhesiveness between the adipose tissue-derived multipotent progenitor cells and cells other than these. In addition to the above, cells other than adipose tissue-derived multipotent progenitor cells can be eliminated, for instance, by filter filtration[3] or the like. the purity and yield of the obtained adipose tissue-derived multipotent progenitor cell population increases by eliminating these cells.

In another aspect, the present invention relate to an adipose tissue-derived multipotent progenitor cell obtainable by the method for obtaining an adipose tissue-derived multipotent progenitor cell from an adipose tissue described above. Such an adipose tissue-derived multipotent progenitor cell expresses Islet-1, as described above.

In a further aspect, the present invention relates to a cell population containing an adipose tissue-derived multipotent progenitor cell obtainable by the method for obtaining an adipose tissue-derived multipotent progenitor cell from an adipose tissue described above. Such a cell population, in substance, does not contain undesirable adipose tissue-derived cells such as erythrocytes and vascular endothelial cells, but may contain cells that are effective for the maintenance/differentiation and the like of the adipose tissue-derived multipotent progenitor cells, such as, feeder cells.

In one aspect, the present invention relates to a method for obtaining a hepatic lobule-like cell cluster from an adipose tissue-derived cell, comprising culturing adipose tissue-derived cells. The present invention is exceptionally excellent on the point that, a cell population similar to a hepatic lobule, which is the minimum functional unit of the liver, can be produced. Adipose tissue-derived cells refers to cells or cell population obtained from a visceral adipose tissue or a subcutaneous adipose tissue, or to cells or cell population induced to differentiate from stem cells such as mesenchymal hepatocytes[4] and ES cells and similar to cells contained in an adipose tissue in an organism. Normally, adipose tissue-derived cells refer to any or all of adipose tissue-derived stem cells, adipose tissue-derived interstitial cells, above-mentioned adipose tissue-derived multipotent progenitor cells, adipose progenitor cells or cells similar to these, or a cell population containing a mixture comprising all or a portion thereof. Adipose tissue-derived cell can be obtained from adipose tissues and the like by means/method well known to those skilled in the art. In addition, the obtained adipose tissue-derived cell may be grown using means/method well known to those skilled in the art, for instance, to stabilize the phenotype. The adipose tissue-derived cells may be grown by culturing the adipose tissue-derived cells in a culture medium containing dexamethasone and ascorbic acid, for instance, in a 60% DMEM (low glucose) and 40% MCDB201 culture medium added with ITS (10.0 mg/L insulin, 5.5 mg/L transferrin, 6.7 ng sodium selenite), 1 nM dexamethasone, 0.1 mM ascorbic acid, 10 ng/mL rhEGF, and 5% FCS, in an incubator such as fibronectin-coated dish.

The animal species from which the adipose tissue-derived cell is derived are not limited in particular, and are preferably, for instance, mammals including mouse, rat, rabbit, dog, cat, cow, horse, monkey and the like, and more preferably human. It is more desirable to use an adipose tissue-derived cell from an identical animal species or an identical individual to the animal species in which a disease is to be prevented or treated using the obtained hepatic lobule-like cell cluster. Since adipose tissues are present in sufficient quantities in organisms and are obtained relatively readily, the present invention is exceptionally excellent compared to, for instance, methods in which hepatic lobules are obtained from limited materials such as corpses, and the like. For instance, by carrying out the above-mentioned method of the present invention using self-derived adipose tissue-derived cells and autografting the obtained hepatic lobule-like cell cluster, diseases that occur due to a decrease in liver functions, such as hepatic cirrhosis, can be treated without fearing a rejection reaction.

Hepatic lobule-like cell cluster refers to hepatic lobule inside an organism and to cell population having similar function/morphology thereto, including, for instance, hepatocyte, biliary tract epithelial cell, endothelial cell, Kupffer cell, hepatic stellate cell and the like. Compared to individual hepatocytes, the hepatic lobule-like cell cluster of the present invention is exceptionally excellent on the point that a sufficient quantity of secretory protein can be produced, the point that it has high metabolic capability, on the point that it has high detoxification capability, and the like. In addition, it also has the advantage of being easily used, for example, in purposes such as grafting or the like, by causing a cell population to be formed.

It is desirable that the acquisition method of hepatic lobule-like cell cluster from adipose tissue-derived cell of the present invention comprises as an important step the step of causing a hepatic lobule-like cell cluster to be formed from an undifferentiated cell. It is desirable that the acquisition method of hepatic lobule-like cell cluster from adipose tissue-derived cell of the present invention further comprises as an important step the step of obtaining an undifferentiated cell from adipose tissue-derived cells. These steps may be carried out one after the other or may be carried out in parallel.

Undifferentiated cell refers to a cell that is capable of differentiating into diverse cells, for instance, hepatic progenitor cell, pancreatic progenitor cell, cardiac muscle progenitor cell, vascular endothelial progenitor cell, osteoblast, chondroblast and the like. The step of obtaining an undifferentiated cell may further comprise the step of growing the obtained undifferentiated cell. By growing the undifferentiated cell, increasing the formation efficiency of the hepatic lobule-like cell cluster, increasing the number of hepatic lobule-like cell cluster, and the like, are possible. The step of obtaining the undifferentiated cell may be carried out using known methods such as, for instance, sorting, MACS, method by antigen-antibody reaction such as rosette forming method, density gradient method, method of selecting based on morphology and single cell cloning, or may be carried out by culturing the adipose tissue-derived cell in a suspended state, causing an adiposphere to be formed. Since it allows already differentiated cell to be killed and undifferentiated cell to survive/grow, culturing the adipose tissue-derived cell in a suspended state, causing an adiposphere to be formed, is preferred. Regarding culturing in a suspended state, a description will follow. Here, an adiposphere is defined as a spheroid containing undifferentiated cell as the principal constituent. Since formation of adiposphere and the subsequent differentiation into a hepatic lobule-like cell cluster may occur sequentially or coincidentally, an adiposphere may contain in addition to undifferentiated cell, hepatocyte, biliary tract epithelial cell, endothelial cell, Kupffer cell, hepatic stellate cell and the like.

The step of obtaining hepatic lobule-like cell cluster is carried out by culturing undifferentiated cell in a culture medium containing, for instance, fibroblast growth factor, hepatocyte growth factor, oncostatin M, epithelial growth factor, and dimethylsulfoxide; preferably, such as step is carried out by culturing the undifferentiated cell in a suspended state. Culturing in suspension allows a cell population having a similar morphology to a hepatic lobule inside an organism to be obtained more readily. Culture of undifferentiated cell in suspended state means placing and culturing the cell in a freed state by preventing or suppressing adhesion to the culture container. Suspension of a cell can be carried out by a variety of well known means/methods. For instance, cells may be placed in a suspended state using a culture container or apparatus treated to prevent or suppress adhesion of cells or made with such materials that prevent or suppress adhesion of cells. As culture container or apparatus, low binding culture containers or the like exist, such as siliconized culture container (for instance, siliconized flask) or low binding culture dish (for instance, HydroCell (CellSeed)). Or cells may be cultured in a suspended state using the hanging drop culture method. In addition, well known means/method may be used in combination suitably at suspension starting time point or to continue suspension. As examples of such means/method, freeing cells with an enzyme or a chelator such as trypsin/EDTA, collagenase and Cell Dissociation Buffer (GIBCO Invitrogen), scraping off cells physically using a scraper] or the like, or methods whereby cells are cultured with a temperature responsive culture equipment [5] for cell recovery (for instance, RepCell (CellSeed)), then, detaching the cells by incubation at for instance, 20° C. for 30 minutes, and the like, exist. The above-mentioned hepatic lobule-like cell cluster is formed by culturing undifferentiated cell in a suspended state.

In another aspect, the present invention relates to a hepatic lobule-like cell cluster obtainable by the above-mentioned method. As described above, the hepatic lobule-like cell cluster of the present invention contains a hepatocyte. For instance, carrying out the above method using cells collected from the adipose tissue of a subject, or a similar to the subject, having a disease that occurs due to a decrease in liver function such as hepatic cirrhosis or predisposition therefor, and grafting the obtained hepatic lobule-like cell cluster to the subject allow diseases that occur due to a decrease in liver function such as hepatic cirrhosis to be treated or prevented, and the like.

In a further aspect, the present invention relates to hepatocyte contained in the hepatic lobule-like cell cluster obtainable by the above method.

In an even further aspect, the present invention relates to a medicinal composition for preventing or treating a disease that occurs due to a decrease in liver function, containing a hepatic lobule-like cell cluster obtainable by the above method and/or a hepatocyte contained in such a hepatic lobule-like cell cluster. A disease that occurs due to a decrease in liver function includes, disease that occurs due not only to a decrease but also to insufficiency in liver function, for instance, hepatitis, hepatic cirrhosis, liver cancer, hepatic insufficiency, drug liver damage, alcoholic liver damage, congenital metabolic anomaly, cholestatic liver damage and the like. In the medicinal composition of the present invention, the hepatic lobule-like cell cluster or the hepatocyte may be suspended in a suitable solution such as PBS. Also, the medicinal composition of the present invention may contain, in addition to the hepatic lobule-like cell cluster or hepatocyte, a substance that promotes grafting thereof to liver, liver function improvement drug, suitable additive, diluent and the like.

In another further aspect, the present invention relates to use of hepatic lobule-like cell cluster obtainable by the above method and/or hepatocyte contained in such a hepatic lobule cell population, for the preparation of a medicinal product for preventing or treating a disease that occurs due to a decrease in liver function.

In a different aspect, the present invention relates to a method for the treatment or prevention of a disease that occurs due to a decrease in liver function comprising administering a subject with the hepatic lobule-like cell cluster obtainable by the above-mentioned culture method and/or hepatocyte contained in such a hepatic lobule-like cell cluster. From the point of rejection reaction and the like, a hepatic lobule-like cell cluster or hepatocyte obtainable from an identical species or autologous adipose tissue-derived cell is used preferably in the present invention. Hepatic lobule-like cell cluster or hepatocyte may be grafted or injected, for instance, under the renal capsule[6], via portal vein, inside the liver, inside the great omentum, side the peritoneal cavity, inside the spleen, under the skin and the like. The subject may be any one; it may be a human subject, or it may be a subject other than human, for instance, a mammal such as mouse or monkey. The administration quantity, administration frequency and the like of the hepatic lobule-like cell cluster or hepatocyte are selected suitably according to a variety of factors such as, for instance, the state of the subject, and the degree of seriousness of the disease.

In addition, the present invention relates to a method for decreasing the blood concentration of bilirubin comprising administering a hepatic lobule cell population and/or a hepatocyte contained in such a hepatic lobule-like cell cluster. Such a method may be performed either in vitro or in vivo.

In another further aspect, the present invention relates to a method for screening for a substance that promotes formation of hepatic lobule, comprising adding a candidate substance to the culture medium when culturing an adipose tissue to obtain a hepatic lobule-like cell cluster, and showing that the candidate substance is a substance that promotes formation of hepatic lobule when formation of hepatic lobule-like cell cluster has been promoted compared to formation in a system not containing the candidate substance. As described above, since a hepatocyte is contained in the hepatic lobule-like cell cluster, such a method also comprises a method for screening for a substance that promotes differentiation into hepatocyte. As candidate substances, many exist and, for instance, analogs or derivatives of basic fibroblast growth factor, hepatocyte growth factor or oncostatin M, and the like, may be cited, without being limited to these. The addition of a candidate substance to the culture medium when obtaining a hepatic lobule-like cell cluster from an adipose tissue may be carried out once or several times at either or both of the step of obtaining an undifferentiated cell from an adipose tissue-derived cell and the step of obtaining a hepatic lobule-like cell cluster from an undifferentiated cell.

The formation of hepatic lobule-like cell cluster can be checked, for instance, by measuring the number of formed hepatic lobule-like cell clusteres by microscopic observation, by quantifying α-fetoprotein, albumin and the like secreted in the culture supernatant, for instance, using ELISA, by measuring the expression of genes such as of α-fetoprotein, albumin, CYP1B1, glutamine synthase, keratin 18 and keratin 19 by quantitative PCR, or by measuring a marker substance of which the expression is known to decrease [7] or increase accompanying the differentiation into/formation of hepatic lobule, for instance, transthyretin, α1-anti-trypsin, tyrosine aminotransferase, glucose-6-phosphatase and the like, by quantitative PCR or ELISA or the like.

Consequently, in a further aspect, the present invention relates to a substance promoting formation of hepatic lobule, obtainable by the above-mentioned screening method. The number of the obtained hepatic lobule-like cell clusteres may be increased, or the speed of formation of hepatic lobule-like cell cluster may be increased, by using such a substance in the method for obtaining a hepatic lobule-like cell cluster from an adipose tissue-derived cell of the present invention. Or, such a substance may be used in the treatment or prevention of a disease that occurs due to a decrease in liver function.

Another further aspect of the present invention relates to a method for screening for a substance that inhibits formation of hepatic lobule, comprising adding a candidate substance to the culture medium when culturing an adipose tissue-derived cell to obtain a hepatic lobule-like cell cluster, and showing that the candidate substance is a substance that inhibits formation of hepatic lobule when formation of hepatic lobule-like cell cluster has been inhibited compared to formation in a system not containing the candidate substance. As described above, since a hepatocyte is contained in the hepatic lobule-like cell cluster, such a method also comprises a method for screening for a substance that inhibits differentiation into hepatocyte. As candidate substances, many exist and, for instance, analogs or derivatives of drugs having hepatotoxicity such as carbon tetrachloride and phenobarbital, and the like, may be cited, without being limited to these. A substance obtainable by such a screening method is sought to be suited for the treatment or prevention of a disease occurring due to liver hyperfunction. Regarding addition of the candidate substance to the culture medium and means/method for evaluating formation of hepatic lobule-like cell cluster are as described above.

Consequently, in a further aspect, the present invention relates to a substance inhibiting formation of a hepatic lobule, obtainable by the above-mentioned screening method.

In yet another further aspect, the present invention relates to a kit used in the above-mentioned method for screening for a substance that accelerates or suppresses the formation of a hepatic lobule. The kit of the present invention may contain cell acquisition means from an adipose tissue, a culture medium, a culture container, as well as means for checking the formation of the hepatic lobule-like cell cluster, and the like. Normally, handling instructions are included with the kit. Using such a kit allows the above-mentioned screening to be carried out rapidly and readily.

In another aspect, the present invention relates to a method for screening for a substance that elevates the activity of a hepatic lobule, comprising culturing in a medium containing a candidate substance a hepatic lobule-like cell cluster obtained by culturing an adipose tissue-derived cell, and showing that the candidate substance is a substance that elevates the activity of a hepatic lobule when the activity of the hepatic lobule-like cell cluster has been increased compared to the activity in a system not containing the candidate substance. Activity of a hepatic lobule refers to detoxification action, protein synthesis capability, metabolic action, and the like, of the hepatic lobule.

Elevation of the activity of a hepatic lobule-like cell cluster can be checked, for instance, by quantifying α-fetoprotein, albumin and the like secreted in the culture supernatant using ELISA or the like, and from the increase or decrease of such protein quantities, or by measuring the expression of genes such as of α-fetoprotein, albumin, CYP1B1, glutamine synthase, keratin 18 and keratin 19 by quantitative PCR, and from the increase or decrease of the expression of such genes. As candidate substances, many exist and, for instance, analogs or derivatives of basic fibroblastic growth factor, hepatocyte growth factor, or oncostatin M, and the like, may be cited, without being limited to these. Addition of candidate substance into the culture medium may be carried out once of multiple times.

Consequently, in another aspect, the present invention relates to a substance that elevates the activity of a hepatic lobule, obtainable by the above-mentioned screening method. The activity of the obtained hepatic lobule-like cell cluster may be increased by using such a substance in the method for obtaining a hepatic lobule-like cell cluster from an adipose tissue-derived cell of the present invention. Or, such a substance may be used in the treatment or prevention of a disease that occurs due to a decrease in liver function.

In another aspect, the present invention relates to a method for screening for a substance that diminishes the activity of a hepatic lobule, comprising culturing in a medium containing a candidate substance a hepatic lobule-like cell cluster obtained by culturing an adipose tissue-derived cell, and showing that the candidate substance is a substance that diminishes the activity of a hepatic lobule when the activity of the hepatic lobule-like cell cluster has been diminished compared to the activity in a system not containing the candidate substance. As candidate substances, many exist and, for instance, analogs or derivatives of carbon tetrachloride an phenobarbital, and the like, may be cited, without being limited to these. Regarding addition of the candidate substance into the culture medium, means/method for evaluating the activity of hepatic lobule-like cell cluster, the descriptions are as above.

Consequently, in another aspect, the present invention relates to a substance that diminishes the activity of a hepatic lobule, obtainable by the above-mentioned screening method.

In yet another further aspect, the present invention relates to a kit used in the above-mentioned method for screening for a substance that elevates or diminishes the activity of a hepatic lobule. The kit of the present invention may contain cell acquisition means from an adipose tissue, a culture medium, a culture container, as well as means for checking the activity of the hepatic lobule-like cell cluster, and the like. Normally, handling instructions are included with the kit. Using such a kit allows the above-mentioned screening to be carried out rapidly and readily.

In addition, cardiac myoblasts are provided by the present invention in sufficient amounts to constitute a sheet. Consequently, in one aspect, the present invention provides a sheet that contains cardiac myoblasts. Herein, a cardiac myoblast refers to a cell that has been directed to differentiate into a cardiac myocyte, which is a cell expressing α-cardiac actin (α-CA) and Myosin Light Chain (MLC). The animal species from which the cardiac myoblast is derived are not limited in particular, and are preferably, for instance, mammals including human, mouse, rat, rabbit, dog, cat, cow, horse, monkey and the like, and more preferably human. Or, the species similar to or identical to the subject in which such sheet containing cardiac myoblasts is applied is desirable. For instance, by grafting a subject with a sheet containing cardiac myoblasts derived from the same species or the same animal as the subject, treating severe cardiac failure, or the like, becomes possible, without fearing a rejection reaction.

A sheet containing cardiac myoblasts refers to a cell population containing cardiac myoblasts as essential constituent. In the sheet, the cardiac myoblast may be contained in either form of a mono-layer or a multi-layer. Having the morphology of a sheet allows for ease of handling when used for grafting or the like. Constituents of the sheet other than cardiac myoblasts may be any, for instance, adipose tissue-derived stem cells, cardiac myocytes, cell scaffolds, vascular endothelium, matrix, and the like, may be cited. The size and thickness of the sheet may be selected suitably according to a variety of conditions such as the extent of the injured area.

The proportion of cardiac myoblasts contained in a sheet is not limited in particular and may be selected suitably according to a variety of conditions such as, for instance, the state of the subject in which the sheet is applied. The proportion is, for instance, 5%, 10%, 20%, 30%, 40%, 50%, 60%, 70%, 80%, 90%, 95%, 100% and the like. The proportion of cardiac myoblasts may be determined by quantifying α-CA or MLC, which are cardiac myoblast marker genes, using means known to those skilled in the art, for instance, quantitative RT-PCR.

The function of the sheet of the present invention can be checked by well known methods, for instance, by grafting a sheet to a subject, and by echography of the cardiac function of the grafted subject, or by measuring the diameter at end-diastole (LVDd), the diameter at end-systole (LVDs), the left ventricular ejection fraction (% EF) or the left ventricular internal diameter shortening fraction (% FS) and the like.

In another aspect, the present invention provides a method for obtaining cardiac myoblasts, comprising culturing an adipose tissue-derived stem cell. According to the method, cardiac myoblasts can be obtained in large amounts from an adipose tissue-derived stem cell. The method may comprise the step of obtaining an adipose tissue-derived stem cell from an adipose tissue-derived cells. An adipose tissue-derived stem cell refers to a cell, which is a cell that can differentiate into a variety of cell lines such as of the endoderm, mesoderm and ectoderm, and includes adipose tissue-derived multipotent progenitor cell (ADMPC), which expresses Islet-1, a marker for the absence of differentiation. The animal species from which the adipose tissue-derived stem cell is derived are not limited in particular, and are preferably, for instance, mammals including human, mouse, rat, rabbit, dog, cat, cow, horse, monkey and the like, and more preferably human. Or, the species similar to or identical to a subject to be treated with cardiac myoblasts obtained from such adipose tissue-derived stem cell is desirable.

Preferably, the method for obtaining cardiac myoblasts of the present invention is one that comprises the step of culturing an adipose tissue-derived stem cell in the presence of a DMSO or OP9 culture supernatant. By culturing an adipose tissue-derived stem cell under such condition, the cell may differentiate and/or be induced into a cardiac myoblast. The culture medium used in such culture may be selected suitably. Such a culture medium may be one containing a variety of factors such as, for instance, retinoic acid, BMP2, BMP4, TGFβ2, HGF, bFGF, thyroxine, oxytocin or fatty acid concentrate. Differentiation into cardiac myoblast can be checked by measuring the expression of a cardiac myoblast marker such as, for instance, α-CA or MLC by RT-PCR.

Consequently, in a further aspect, the present invention provides cardiac myoblast obtainable by the method for obtaining cardiac myoblasts described above. Such cardiac myoblasts can be used in treatment of cardiac diseases such as myocardial infarction and cardiac myopathy, or can be used as materials for a sheet containing cardiac myoblasts.

In another aspect, the present invention provides a method, which is a method for obtaining a sheet containing cardiac myoblasts, comprising the following steps: (a) causing an adipose tissue-derived stem cell to differentiate into a cardiac myoblast, then, (b) causing a sheet containing cardiac myoblasts to form. These steps may be carried out one after the other or may be carried out in parallel. According to such a method, a sheet containing cardiac myoblasts can be obtained readily and efficiently. The step of causing an adipose tissue-derived stem cell to differentiate into a cardiac myoblast is as described above.

The step of causing a sheet containing cardiac myoblasts to form from a cardiac myoblast may be achieved by means or method known by those skilled in the art. Preferably, the step may be achieved by causing a cardiac myoblast to multiply in an attached state to form a cell population and then peeling the formed cell population. The number of cardiac myoblasts used and culture time may be selected suitably according to a variety of conditions, such as, the extent of the obtained sheet and the number of cardiac myoblasts contained in the sheet. For instance, a sheet may be obtained by culturing $10^5$ to $10^6$ cardiac myoblasts for 24 to 72 hours. Peeling of the cell population may be carried out by a variety of means, for instance, physical stimulation. Or, the cardiac myoblasts may be cultured in a temperature-sensitive culture dish and incubated for instance at 20° C. or below to peel the cell population.

Consequently, in a further aspect, the present invention relates to a sheet containing cardiac myoblasts, obtainable by the method for obtaining a sheet containing cardiac myoblasts described above. Such a sheet containing cardiac myoblasts can be used in the treatment of cardiac diseases such as myocardial infarction and cardiac myopathy.

In another aspect, the present invention relates to a method for treating and/or preventing a disease occurring due to a decline in the function of cardiac muscle, comprising grafting a sheet containing cardiac myoblasts or cardiac myoblasts to a subject. Diseases occurring due to a decline in the function of cardiac muscle are, for instance, acute myocardial infarction, old myocardial infarction, ischemic myocardial infarction, dilated cardiac myopathy, congenital cardiac disease and the like. Grafting to a subject may be carried out by methods known to those skilled in the art. It may be carried out, for instance, by grafting a sheet containing cardiac myoblasts to a region where function of cardiac muscle decreased, or by grafting cardiac myoblasts via the coronary artery. The size and thickness of the sheet to be grafted, the number of cardiac myoblasts contained in the sheet, and the number of cardiac myoblasts may be selected suitably according to a variety of conditions such as the state of the subject and the extent of the injured region.

Consequently, in another aspect, the present invention provides a composition containing a sheet containing cardiac myoblasts or cardiac myoblasts for treating and/or preventing disease caused by a decrease in cardiac function. Such a composition may contain, in addition to the sheet or the cardiac myoblasts, for instance, PBS, a culture medium, a substance that promotes grafting, a cardiac function improver, a growth factor, a proliferation factor and the like.

In another aspect, the present invention relates to a method, which is a method for screening a substance that promotes differentiation into cardiac myoblast, comprising the following steps:

(a) causing an adipose tissue-derived stem cell to differentiate into a cardiac myoblast in a culture medium containing a candidate substance;

(b) checking the differentiation of the adipose tissue-derived stem cell into cardiac myoblast, and showing that the candidate substance is a substance that promotes differentiation into cardiac myoblast when the differentiation has been promoted compared to the differentiation when the adipose tissue-derived stem cell is cultured in a culture medium not containing the candidate substance. As candidate substances, many exist and analogs or derivatives of, for instance, retinoic acid, BMP2, BMP4, TGFβ2, HGF, bFGF, thyroxine, or oxyton[8], and the like, may be cited, without limiting to these. Differentiation of adipose tissue-derived stem cell into cardiac myoblast is as described above. Differentiation into cardiac myoblast can be checked by a variety of methods, for instance, by measuring the expression of a cardiac myoblast marker such as α-CA or MLC by RT-PCR.

Consequently, in a further aspect, the present invention relates to a substance that promotes differentiation into cardiac myoblast, which can be obtained by the method for screening for a substance that promotes differentiation into cardiac myoblast described above. The substance may be used in the production method for the cardiac myoblast and sheet containing cardiac myoblasts described above to increase the number of the obtained cardiac myoblasts and sheets. Or, such a substance may be used in the treatment or prevention of a disease caused by a decrease in cardiac function.

In another aspect, the present invention relates to a method, which is a method for screening a substance that inhibits differentiation into cardiac myoblast, comprising the following steps:

(a) causing an adipose tissue-derived stem cell to differentiate into a cardiac myoblast in a culture medium containing a candidate substance;

(b) checking the differentiation of the adipose tissue-derived stem cell into cardiac myoblast, and showing that the candidate substance is a substance that inhibits differentiation into cardiac myoblast when the differentiation has been inhibited compared to the differentiation when the adipose tissue-derived stem cell is cultured in a culture medium not containing the candidate substance. As candidate substances, many exist and analogs or derivatives of, for instance, noggin, and the like, may be cited, without limiting to these.

Consequently, in a further aspect, the present invention relates to a substance that inhibits differentiation into cardiac myoblast, which can be obtained by the method for screening for a substance that inhibits differentiation into cardiac myoblast described above. The substance may be used in the treatment or prevention of a disease caused by an elevation in cardiac function.

In addition, the present invention relates to a kit for screening for a substance that promotes or inhibits differentiation into cardiac myoblast. The kit of the present invention may contain an adipose tissue-derived stem cell, a culture medium, a culture container, as well as means for checking differentiation into cardiac myoblast and the like. Normally, handling instructions are included with the kit. Using such a kit allows the above-mentioned screening to be carried out rapidly and readily.

In another aspect, the present invention provides a method, which is a method for screening for a substance that promotes or inhibits formation of a sheet containing cardiac myoblasts, comprising the following steps:

(a) causing an adipose tissue-derived stem cell to differentiate into a cardiac myoblast in a culture medium containing a candidate substance; or (b) causing a sheet containing cardiac myoblasts to formation in the presence of a candidate substance;

(c) checking the formation of a sheet containing cardiac myoblasts, and showing that the candidate substance is a substance that promotes or inhibits formation of a sheet containing cardiac myoblasts when the formation has been promoted or inhibited compared to that formed in a system not containing the candidate substance. The method for checking the formation of sheet is as described above. The addition of candidate substance may be carried out in both steps (a) and (b) described above, or may be carried out in either one.

Consequently, in a further aspect, the present invention relates to a substance that promotes or inhibits formation of a sheet containing cardiac myoblasts, which can be obtained by the screening method for a substance that promotes or inhibits formation of a sheet containing cardiac myoblasts described above.

In addition, the present invention relates to a kit for screening for a substance for promoting or inhibiting formation of a sheet containing cardiac myoblasts described above.

Hereinafter, the present invention will be described concretely and in detail showing examples; however the examples shall not be interpreted as limiting the present invention.

EXAMPLE 1

Collection of Adipose Tissue from Human Subject

Excessive adipose tissue was extracted during gastric cancer operation from ten subjects (four males and six females) from whom informed consents were received. The protocol was according to Osaka University Graduate School of Medicine Review Boards for Human Research. All subjects were fasted for at least 10 hours. The age of the subjects was 55±5 years (average ±SE; 40 to 60 years range). There were no subject being administered with a steroidal agent or TZD. From the subjects, 1 to 10 g of abdominal subcutaneous (outside of fascial surface) adipose tissue and dorsal mesogastrium adipose tissue.

Isolation and Culture of ADMPC

The adipose tissue was sliced, and then digested in Hank's buffered saline solution (HBSS) containing 0.075% collagenase (Sigma Chemical Co.) for one hour while shaking in a 37° C. water bath. The digestion product was filtered with Cell Strainer (BD Bioscience) and centrifuged at 800 g[9] for 10 minutes. Erythrocytes were eliminated by the density method using Lymphoprep (d=1.077) (Nycomed), and the obtained preadipose tissue-derived multipotent progenitor cell population was cell-plated in DMEM containing 10% fetal bovine serum (Hyclone) [10]. Cells were attached by culturing for 24 hours, washed and then treated with EDTA to obtain ADMPCs. Next, ADMPCs were plated in Culture Medium I: 60% DMEM-low glucose, 40% MCDB201, 10 μg/mL EGF, 1 nM dexamethasone, 100 μM ascorbic acid, and 5% FBS, at a density of 10,000 cell/cm² over human fibronectin coated dishes, subcultured 3 to 5 times, and used in the experiments. The micrograph of ADMPC cultured for 10 days is shown in FIG. 1.

EXAMPLE 2

ADMPC Expression Characteristics

Figure 2:
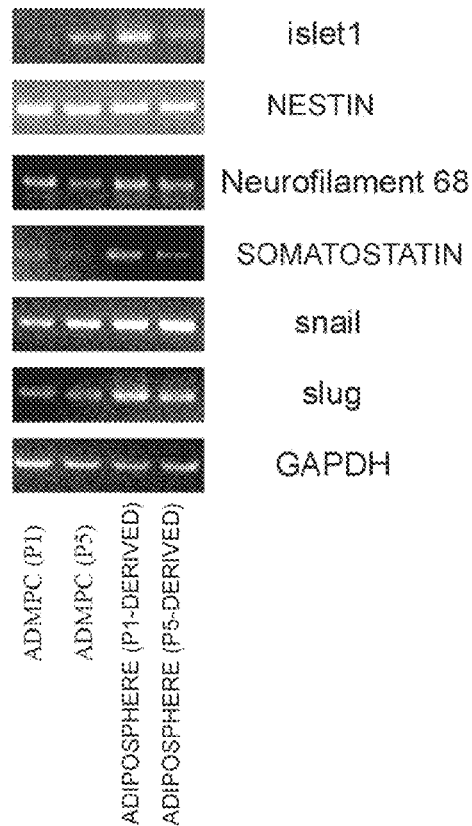
FIG. 2 shows the expression of a neural crest[1] cell-specific marker gene from the results of RT-PCR using ADMPC-derived RNA.
Figure 3:
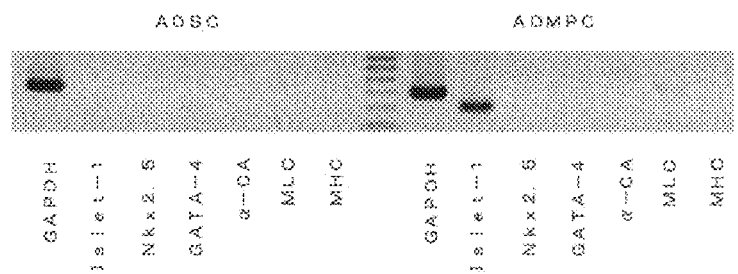
FIG. 3 is an electrophoretic image showing the results of RT-PCR using ADMPC-derived RNA.
Figure 4:
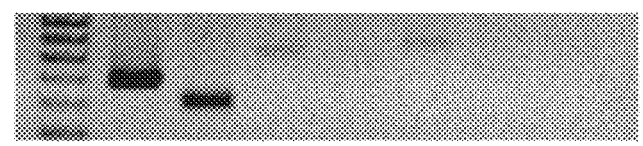
FIG. 4 shows the results of RT-PCR when ADMPC was sub-cultured six times.

Total RNA was isolated from ADMPC and adiposphere, using Mag-Extractor kit (TOYOBO) according to the protocols recommended by the manufacturer. Dnase treatment was carried out on 500 ng of total RNA and cDNA was synthesized using Superscript III reverse transcriptase RNase H (−) (Invitrogen). RT-PCR was carried out for Islet-1, Nkx2.5, GATA-4, α-CA, MLC, MHC, nestin, neurofilament 68, somatostatin, snail, slug, and GAPDH, using KOD-plus (TOYOBO), under the following conditions: 40 cycles of degeneration at 94° C. for 2 minutes, then degeneration at 94° C. for 15 seconds, annealing at predetermined temperature for 30 seconds and elongation at 68° C. for 30 seconds elongation. The annealing temperature and primer sequence of each gene is shown in Table 1. As a control, adipose tissue-derived stem cell (hereinafter referred to as "ADSC") obtained according to methods described in Japanese Translation of PCT Application No. 2005-502352 was used. The obtained amplification products were electrophoresed on a 2% agarose gel. The results are shown in FIG. 2 to FIG. 4. Similarly to adipospheres, ADMPC was suggested to express snail and slug, which are markers of neural crest cells. In addition, ADMPC was shown to express a marker of absence of differentiation, in particular Islet-1, known as a marker for cardiac, hepatic and pancreatic progenitor cells. ADSC did not express Islet-1, which confirms that the obtained ADMPC is a different cell from ADSC.

TABLE 1

| Gene | Primer sequence | SEQ ID | Annealing temperature (° C.) |
|---|---|---|---|
| Islet-1 | GTCAGTGGTGGACCTGACCT | 1 | 60 |
|  | AGGGGAGATTCAGTGTGGTG | 2 |  |
| Nkx2.5 | GGTGGAGCTGGAGAAGACAGA | 3 | 60 |
|  | CGACGCCGAAGTTCACGAAGT | 4 |  |
| GATA-4 | ACCAGCAGCAGCGAGGAGAT | 5 | 60 |
|  | GAGAGATGCAGTGTGCTCGT | 6 |  |
| α-CA | GGAGTTATGGTGGGTATGGGTC | 7 | 60 |
|  | AGTGGTGACAAAGGAGTAGCCA | 8 |  |
| MLC-2v | GCGCCAACTCCAACGTGTTCT | 9 | 60 |
|  | GTGATGATGTGCACCAGGTTC | 10 |  |
| MHC | GGGGACAGTGGTAAAAGCAA | 11 | 60 |
|  | TCCCTGCGTTCCACTATCTT | 12 |  |
| GAPDH | GTCAGTGGTGGACCTGACCT | 13 | 60 |
|  | AGGGGAGATTCAGTGTGGTG | 14 |  |
| nestin | GGCGCACCTCAAGATGTCC | 15 | 60 |
|  | CTTGGGGTCCTGAAAGCTG | 16 |  |
| Neurofilament 68 | ATGAGTTCCTTCAGCTACGAGC | 17 | 60 |
|  | GGGCATCAACGATCCAGAGC | 18 |  |
| somatostatin | GCTGCTGTCTGAACCCAAC | 19 | 60 |
|  | CGTTCTCGGGGTGCCATAG | 20 |  |
| snail | AATCGGAAGCCTAACTACAGCG | 21 | 60 |
|  | GTCCCAGATGAGCATTGGCA | 22 |  |
| slug | AAGCATTTCAACGCCTCCAAA | 23 | 60 |
|  | AGGATCTCTGGTTGTGGTATGAC | 24 |  |

Figure 5:
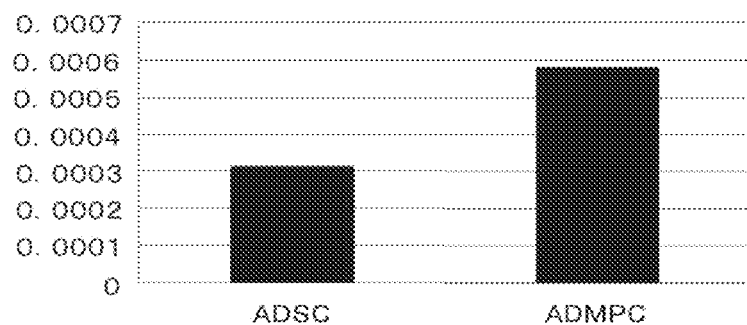
FIG. 5 is a graph showing the amount of expression by quantitative PCR of Sca-1 in ADMPC. The vertical axis represents Sca-1/GAPDH.
Figure 6:
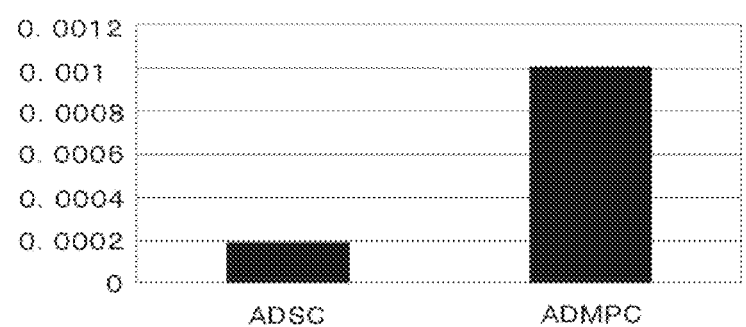
FIG. 6 is a graph showing the amount of expression by quantitative PCR of ABCG2 in ADMPC. The vertical axis represents ABCG2/GAPDH.

In addition, ADMPC was checked for the expression of Sca-1 and ABCG2, which are markers for the absence of differentiation, by carrying out real time PCR with Applied Byosystems[11] 7900 Fast Real-Time PCR system (details will be given below). The TaqMan probes used are shown in Table 2. The results are shown in FIGS. 5 and 6. ADMPC was confirmed to express Sca-1 and ABCG2.

TABLE 2

| Gene name | Reference sequence | Assay ID |
|---|---|---|
| Sca-1 | NM_000332.2 | Hs00165656_m1 |
| ABCG2 | NM_004827.2 | Hs00184979_m1 |

Figure 7:
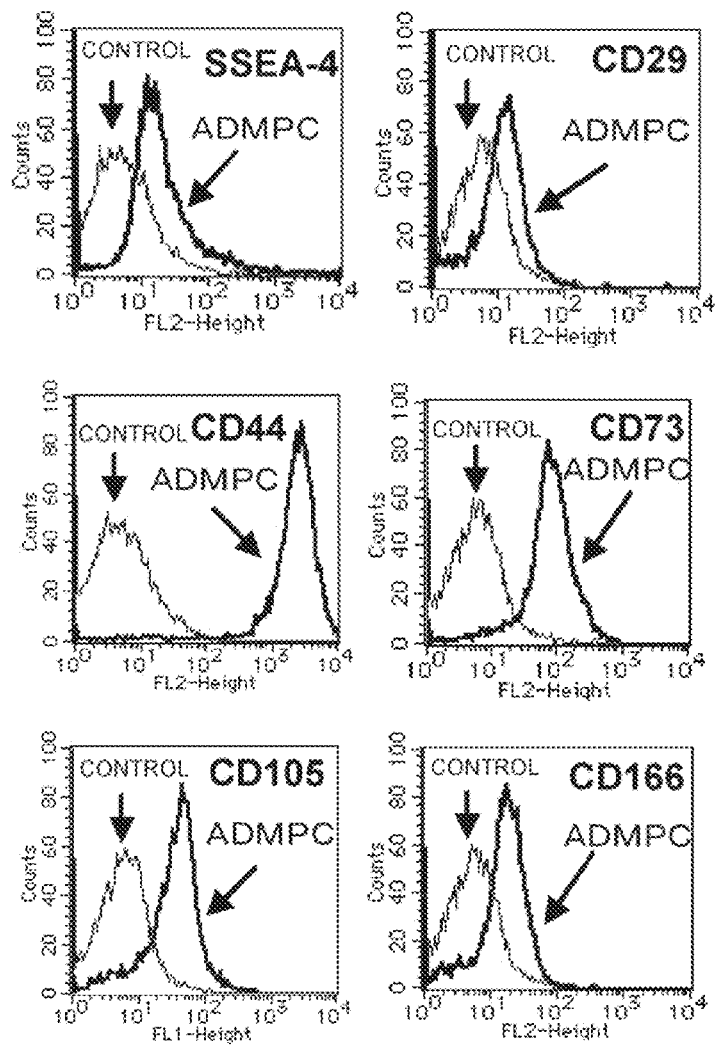
FIG. 7 is the result of FACS analysis showing the expression of SSEA-4, CD29, CD44, CD73, CD105 and CD166 in ADMPC.
Figure 8:
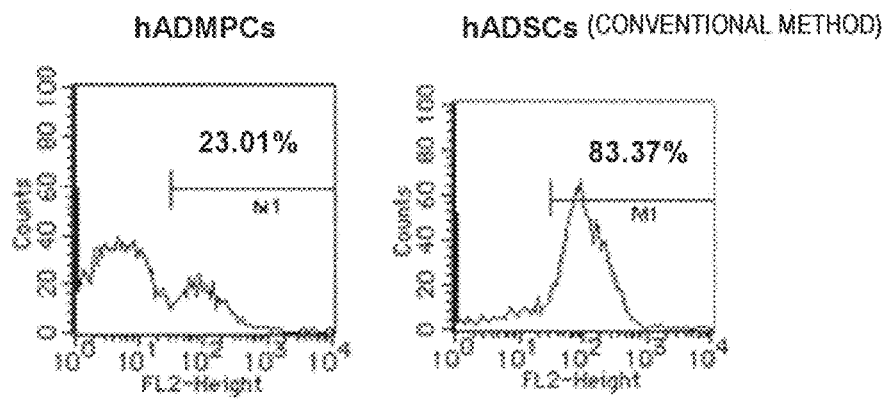
FIG. 8 is the result of FACS analysis showing that fibroblastic contamination is small in ADMPC compared to ADSC from a conventional method.

In order to check additional characteristics of ADMPC, ADMPCs isolated from adipocytes were subjected to FACS. ADMPCs were separated from a culture dish with a 0.5 g/L-trypsin/0.53 mM-EDTA solution and suspended in a Dulbecco's Phosphate-buffered Saline (DPBS, Nacalai Tesque) containing 0.1% FBS. A given quantity ($5 \times 10^5$ cells) was incubated with fluorescein isothiocyanate (FITC)-conjugated mouse monoclonal antibodies against human CD31 (BD PharMingen), CD105 (Ancell) and CD133 (R&D), phycoerythrin (PE)-conjugated mouse monoclonal antibodies against human CD29, CD34, CD45, CD56, CD73, CD166 (BD PharMingen), CD44, or CD166 (Ancell), at 4° C. for 30 minutes. In addition, the incubated cells were incubated with mouse monoclonal antibodies against human SSEA-4, TRA-1-60, TRA-1-81 (Chemicon), ABCG-2, CD117 (BD PharMingen), or fibroblast/epithelial cell (AbD Serotec), as well as non-specific mouse antibody used as negative control, at 4° C. for 30 minutes. After washing with DPBS, the cells were incubated with PE-labeled goat anti-mouse Ig antibody (BD PharMingen), at 4° C. for 30 minutes. After washing three times, the cells were resuspended with DPBS, analysis was carried out by flow cytometry using FACSCalibur flow cytometer and CellQuest Pro software (BD Biosciences). The results are shown in FIG. 7 and FIG. 8. Compared to the control, the expression did almost not vary in ADMPC for the markers of hematopoietic system cell and hematopoietic stem cell (CD45, ABCG-2, CD34, CD133) (Mitchell et al., Stem Cells, 24, 376-85 (2006)) and endothelial cell (CD31), surface antigen c-Kit (CD117), as well as surface markers for given ES cell and EG (embryonic germ) cell (TRA-1-60 and TRA-1-81) (James et al., 1998 and Shamblott et al., Proc. Natl. Acad. Sci. USA 95, 1372613731 (1998)). On the other hand, from FIG. 7, it was observed that the expression was elevated for the surface markers of mesenchymal cell and/or nervous stem cell (CD29, CD44, CD73 and CD105) (Mitchell et al., Stem Cells, 24, 376-85 (2006) and Barry et al., Biochem. Biophys. Res. Commun. 265, 134139 (1999)) and the stage-specific embryonic antigen marker (SSEA-4) (Kannagi et al., EMBO J. 2, 23552361 (1983)). In addition, from FIG. 8, in contrast to 83.4% of cells positive for fibroblast surface antigen (Zuk et al., Mol. Biol. Cell. 13, 4279-4295 (2002)) in ADSC by conventional method, there are only 23% in ADMPC, demonstrating that there is little contamination by fibroblasts. From these, it was shown that ADMPC according to the present invention has high differentiation capability, and furthermore, the method of the present invention allows high purity ADMPC to be obtained.

EXAMPLE 3

Figure 9:
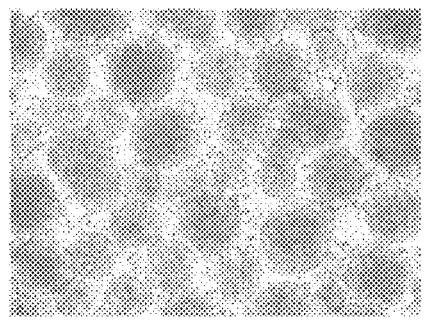
FIG. 9 is a micrograph of pancreatic endocrine cells obtained by causing ADMPC to differentiate.
Figure 10:
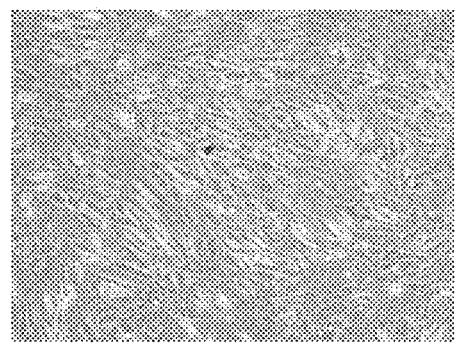
FIG. 10 is a micrograph of hepatocytes obtained by causing ADMPC to differentiate.

Verification of Multipotentiality of ADMPC
1. Differentiation Capability into Pancreatic Cell ADMPCs were differentiated into pancreatic endocrine cells by the methods described in WO 2007/039986. The obtained pancreatic endocrine cells are shown in FIG. 9. The ADMPCs were verified to be capable of differentiating into pancreatic endocrine cells, that is to say, to have functions as pancreatic progenitor cells. In addition, the efficiency of differentiation from such ADMPCs into pancreatic endocrine cells was higher than that from ADSCs (data not shown).
2. Differentiation Capability into Hepatocyte DMSO (0.1%), HGF (10 ng/mL), bFGF (10 ng/mL), and oncostatin M (10 ng/mL), which are known to cause a hepatic progenitor cell to differentiate into a hepatoblast/hepatocyte were added to a Culture Medium I to prepare Culture Medium II. ADMPCs were cultured for 14 days in Culture Medium II to obtain hepatocytes. The obtained hepatocytes are shown in FIG. 10. The ADMPCs were verified to be capable of differentiating into hepatocytes, that is to say, to have functions as hepatic progenitor cell. In addition, the efficiency of differentiation from the ADMPCs into hepatocytes was higher than that from ADSCs (data not shown).

Figure 15:
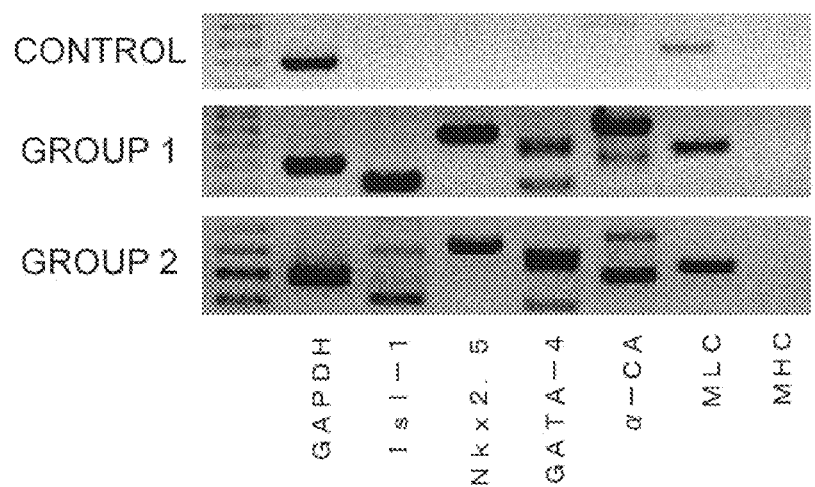
FIG. 15 shows the results of RT-PCR in cells cultured in the presence of DMSO or OP9 culture supernatant.
Figure 16:
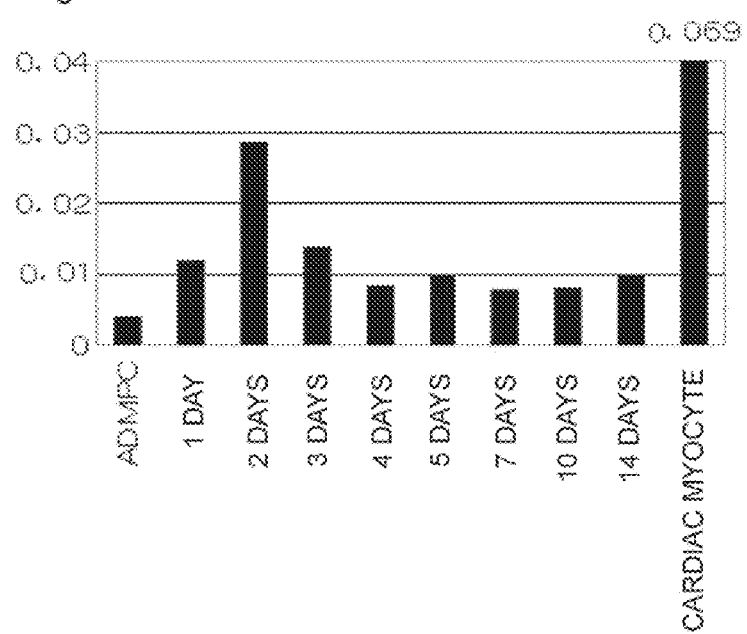
FIG. 16 is a graph showing the expression by quantitative PCR of Nkx2.5 in cells cultured in the presence of DMSO. The vertical axis represents Nkx2.5/GAPDH.
Figure 17:
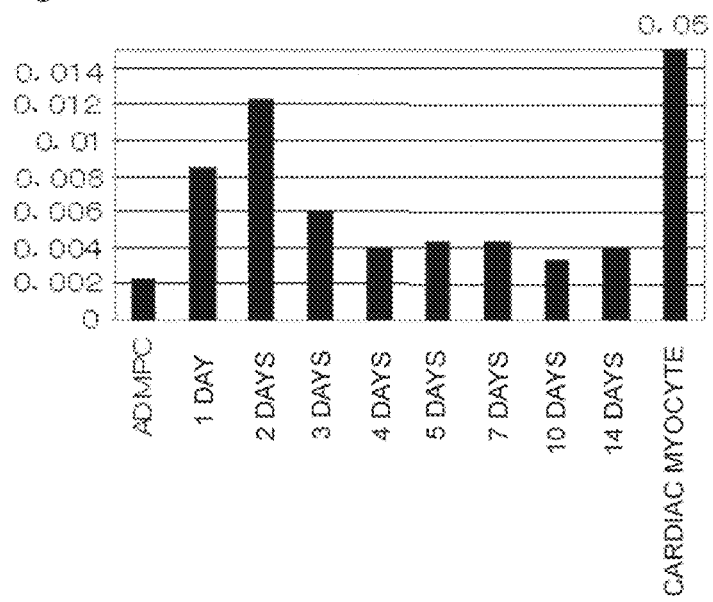
FIG. 17 is a graph showing the expression by quantitative PCR of GATA-4 in cells cultured in the presence of DMSO. The vertical axis represents GATA-4/GAPDH.
Figure 18:
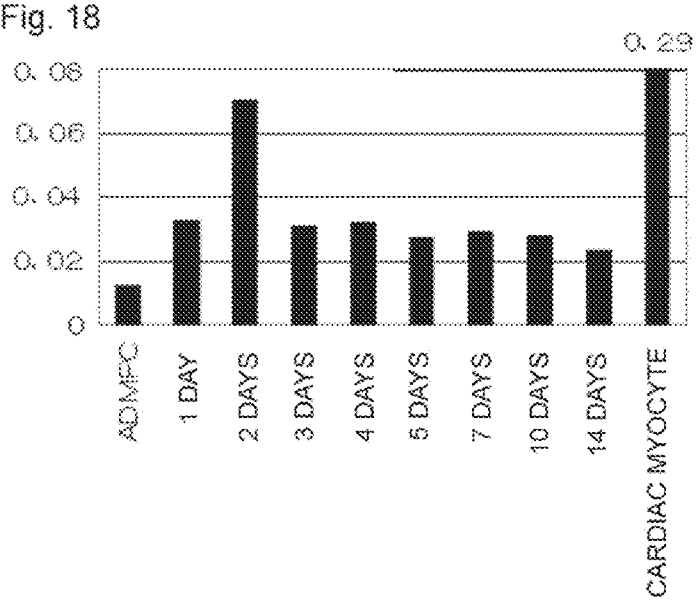
FIG. 18 is a graph showing the expression by quantitative PCR of α-CA in cells cultured in the presence of DMSO. The vertical axis represents α-CA/GAPDH.
Figure 22:
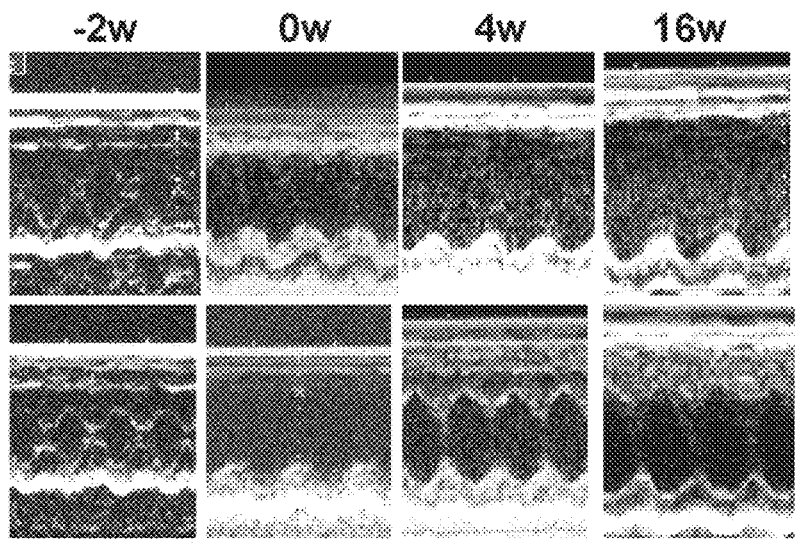
FIG. 22 is an echocardiograph two weeks before grafting, before grafting, and four and 16 weeks after grafting of a sheet containing ADMPC-derived cardiac myoblast. The top row is from MI controls and the bottom row is from a heart grafted with a sheet containing ADMPC-derived cardiac myoblast.
Figure 23:
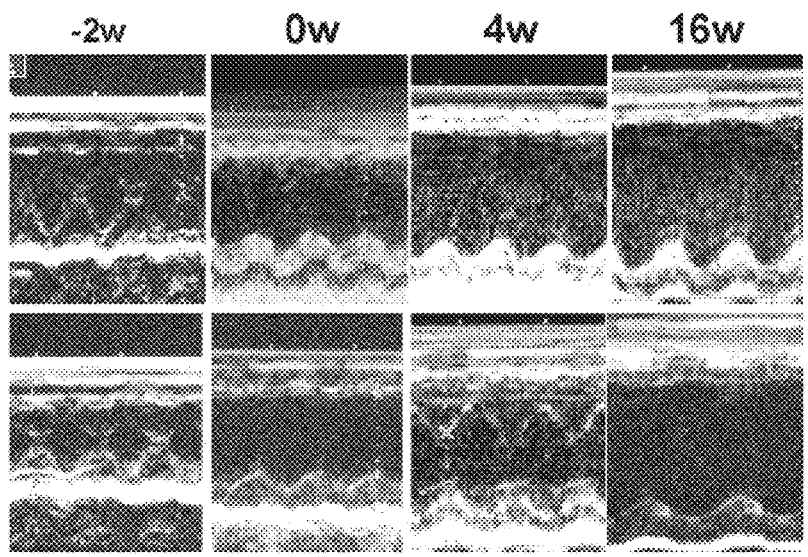
FIG. 23 is an echocardiograph two weeks before grafting, before grafting, and four and 16 weeks after grafting of a sheet containing ADMPC. The top row is from MI controls and the bottom row is from a heart grafted with a sheet containing ADMPC.
Figure 27:
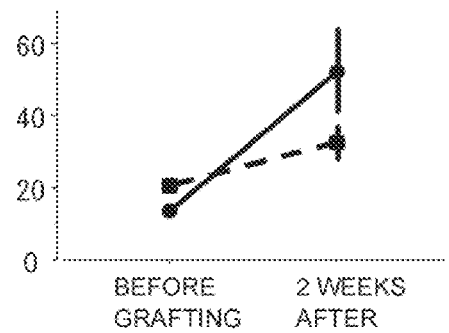
FIG. 27 is a graph showing improvement of % FS of a heart grafted with a sheet containing ADMPC-derived cardiac myoblasts (circle) and a sheet containing ADMPC (square).
Figure 28:
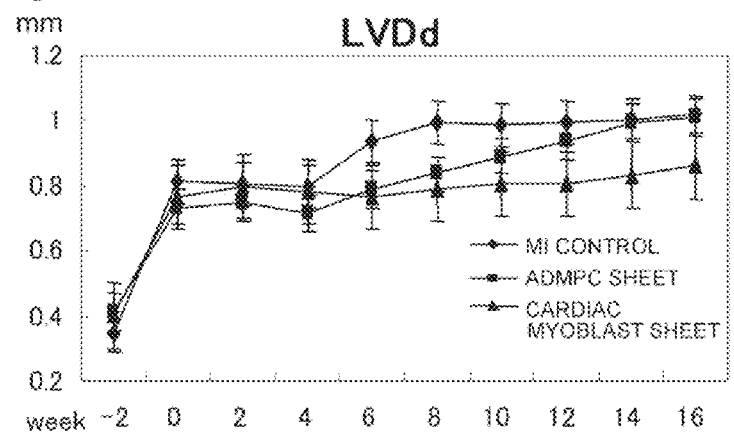
FIG. 28 is a graph showing improvement of LVDs of a heart grafted with a sheet containing ADMPC-derived cardiac myoblasts (triangle) in comparison to a sheet containing ADMPC (square).
Figure 29:
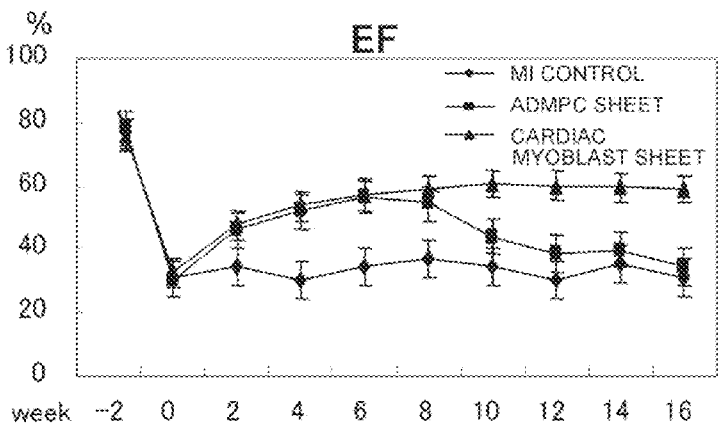
FIG. 29 is a graph showing improvement of % EF of a heart grafted with a sheet containing ADMPC-derived cardiac myoblasts (triangle) in comparison to a sheet containing ADMPC (square).

In addition, real time PCR was performed for the obtained hepatocytes with Applied Byosytems[12] 7900 Fast Real-Time PCR system (the details will be described later) to check the expression of α-fetoprotein (AFP), albumin, CYP1B1 and glutamine synthase, which are markers that show differentiation into hepatocyte. ADMPCs were used as controls. The results are shown in FIGS. 11 to 14. The expression of these genes was verified to be elevated in the obtained hepatocytes.
3. Differentiation Capability into Cardiac Myocyte
Differentiation/Induction from ADMPC to Cardiac Myoblast ADMPCs were cultured in Culture Medium I containing DMSO (Group 1) or OP9 culture supernatant (Group 2) for 14 days and the expression of genes in the obtained cells was checked by RT-PCR as described above. As control, ADMPCs cultured in Culture Medium I were used. The results are shown in FIG. 15. It could be verified that α-CA and MLC, which are markers of cardiac myoblast, were expressed in the cells from Groups 1 and 2, that is to say, ADMPCs were differentiated/induced into cardiac myoblasts.
Examination of Differentiation/Induction Period into Cardiac Myoblast Next, ADMPCs were cultured in the presence of DMSO for 1, 2, 3, 4, 5, 7, 10 and 14 days to check the differentiation into cardiac myoblasts. As controls, ADMPC and cardiac myocyte were used. The results are shown in FIGS. 16 to 20. It was found that culturing in the presence DMSO allowed cardiac myoblasts to be obtained.
Preparation of Sheet Containing Cardiac Myoblasts The obtained cardiac myoblast were cultured in Culture Medium I containing DMSO in a thermosensitive culture dish (CellSeed Inc.) at 37° C. to form a cell population. The cell population was detached by incubating at 20° C. or lower for 30 minutes to obtain a sheet containing cardiac myoblasts (refer to FIG. 21). The obtained sheet was used in the following grafting experiment.
Grafting of Sheet to Myocardial Infarction Model Rat A myocardial infarction model rat was prepared by ligating the coronary artery of a nude rat. Then, an ADMPC-derived sheet containing cardiac myoblasts was grafted to the injured region. Cardiac function was evaluated at two weeks before grafting, before grafting, and two weeks, four weeks and 16 weeks after grafting by measuring the diameter at end-diastole (LVDd), the diameter at end-systole (LVDs), the left ventricular ejection fraction (% EF) and the left ventricular internal diameter shortening fraction (% FS) with echo. As a control, a sheet containing ADMPCs formed as described above was used. The results are shown in FIGS. 22 to 29. Wall motion was observed in rats at 2 weeks and 10 weeks after grafting the sheet containing cardiac myoblasts, showing that cardiac function was remarkably improved. In contrast, in rats grafted with a sheet containing ADMPCs, although wall motion was observed after 2 weeks, it was not observed after 10 weeks. In addition, the LVDd started to extend and the EF decreased at week 8 and later with the sheet containing ADMPCs; in contrast, LVDd and EF were both maintained with the sheet containing ADMPC-derived cardiac myoblast (ADMPC-derived cardiac myoblast is obtained by treating ADMPC in 0.1% DMSO for 48 hours), showing an improvement in cardiac function.

Histological Analysis of Heart Grafted with the Sheet

At 12 weeks and 16 weeks after grafting, rats were sacrificed and the hearts were extracted. The extracted hearts were fixed with a 4% paraformaldehyde solution, and then substituted with ethanol at 70%. The fixed hearts were cut into a width of a few millimeters and solidified with paraffin to prepare blocks. The obtained paraffin blocks were thin-sectioned to 2 μm using a microtome, pasted onto a slide glass and dried. The obtained thin sections were subjected to haematoxylin-eosin staining and immunohistological staining as follows.

A. Haematoxylin-Eosin Staining

Figure 30:
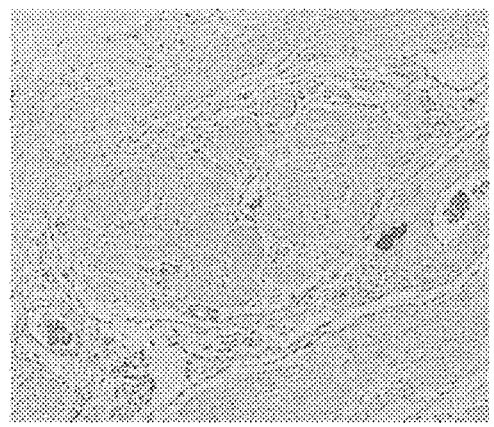
FIG. 30 is a HE staining image (100×) of a heart grafted with a sheet containing cardiac myoblast.
Figure 31:
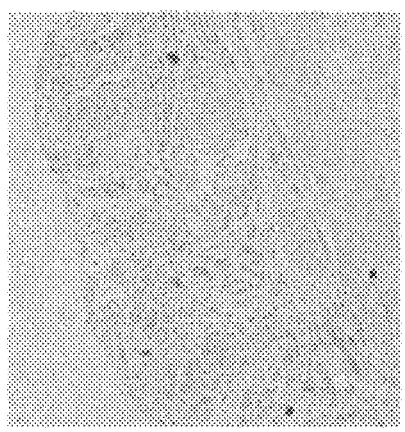
FIG. 31 is a HE staining image (100×) of a heart grafted with a sheet containing ADMPC.
Figure 32:
FIG. 32 is a micrograph (100×) of a heart grafted with a sheet containing cardiac myoblast when immunostained using an anti-human α-CA antibody.
Figure 33:
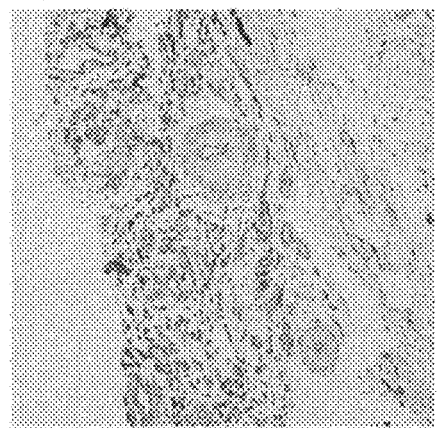
FIG. 33 is a micrograph (100×) of a heart grafted with a sheet containing ADMPC when immunostained using an anti-human α-CA antibody.
Figure 34:
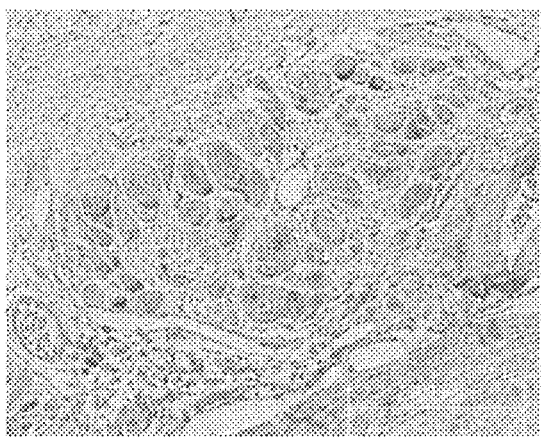
FIG. 34 is a micrograph (100×) of a heart grafted with a sheet containing cardiac myoblast when immunostained using an anti-human MHC antibody.
Figure 35:
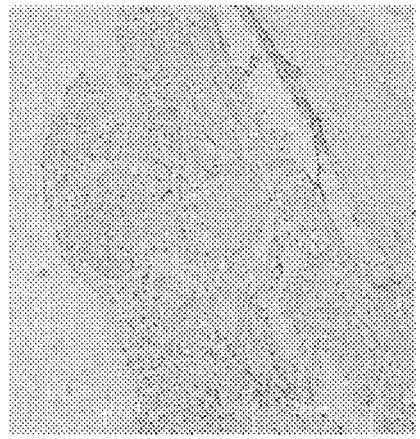
FIG. 35 is a micrograph (100×) of a heart grafted with a sheet containing ADMPC when immunostained using an anti-human MHC antibody.
Figure 36:
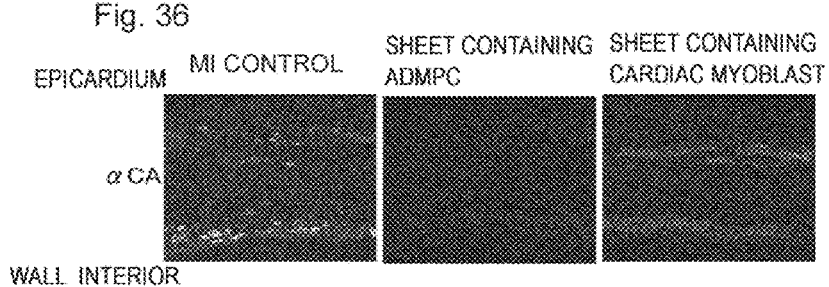
FIG. 36 is a figure showing micrographs of structures of hearts after grafting of sheets containing ADMPC-derived cardiac myoblast and ADMPC when immunostained using an anti-human α-CA antibody.
Figure 37:
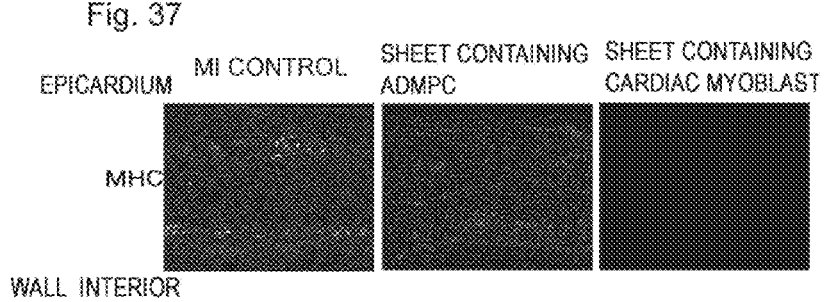
FIG. 37 is a figure showing micrographs of structures of hearts after grafting of sheets containing ADMPC-derived cardiac myoblast and ADMPC when immunostained using an anti-human MHC antibody.
Figure 38:
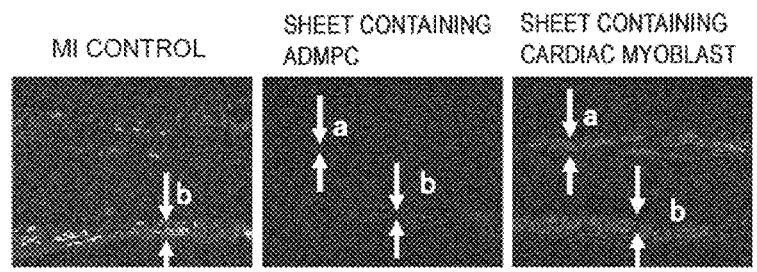
FIG. 38 is a figure representing the thickness of anti-human α-CA antibody-positive regions after grafting sheets containing ADMPC-derived cardiac myoblast and ADMPC.

Thin sections were de-paraffinized and washed with water. Staining with haematoxylin solution was performed for 10 minutes and coloration was performed for 3 minutes in lukewarm water. After rinsing, staining with eosin was performed for 5 minutes. Fractionation and dehydration were performed with alcohol. After clarifying with xylene, mounting was performed, and observation was performed with a microscope. The results are shown in FIGS. 30 and 31. It was verified that the grafted sheet had engrafted.

B. Immunohistological Staining

Thin sections were de-paraffinized and washed with water. Immunostimulation treatment was performed, immersion into TBS-T added with 10% normal goat serum was performed, and blocking was performed at 4° C. for 24 hours. After washing with TBS-T, primary antibody diluted 100-fold with TBS-T added with 10% normal goat serum was added drop-wise to the sample and reacted at 37° C. for one hour. As primary antibodies, anti-human α-cA antibody (American Research Products, Inc), anti-human MHC antibody (Upstate cell signaling solutions) and anti-human HLA-ABC antibody (Hokudo Co., Ltd.) were used. After washing with TBS-T, Simple Stain Rat MAX-PO (Nichirei Bioscience Corp.) was added drop-wise and reacted at room temperature for 30 minutes. After washing with TBS-T, Simple Stain AEC Solution (Nichirei Bioscience Corp.) was added drop-wise and colored while examining under microscope. After washing with water, nuclear staining was carried out by staining with haematoxylin solution for 3 minutes. After washing with water, non-water soluble mounting agent (Nichirei Bioscience Corp.) was added drop-wise, mounting was performed with a cover glass, and observation was carried out with a microscope and a fluorescence microscope. In addition, in order to evaluate the amount that differentiated into cardiac muscle and the amount of remaining cardiac muscle in the region where the sheets containing ADMPC and ADMPC-derived cardiac myoblast were grafted, the thickness of α-CA antibody-positive region was measured. The results are shown in FIGS. 32 to 41. It could be verified that the site where the sheet containing cardiac myoblasts was grafted was HLA-ABC-positive, that is to say, human-derived, expressed α-CA and MHC, was differentiated into cardiac muscle, and that the expression of α-CA was also maintained in the remaining cardiac muscle. Consequently, it was found that the grafted cardiac myoblasts transdifferentiated into cardiac myocytes and that the remaining cardiac muscle was protected.

4. Differentiation Capability into Adipocyte

Figure 43:
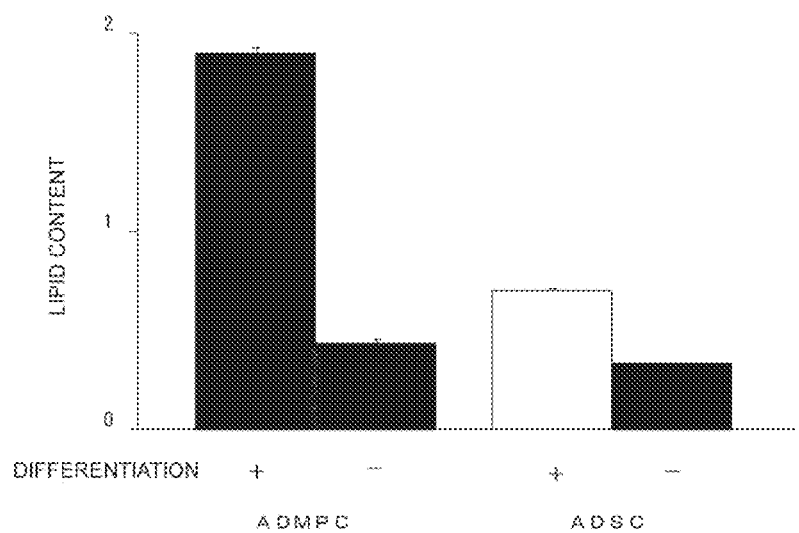
FIG. 43 is a graph showing the content in lipids contained in an adipocyte obtained by causing ADMPC to differentiate. The vertical axis represents lipid content (oil red O content/well).

ADMPCs were cultured using the adipocyte differentiation agent PPAR-γ agonist to be differentiated into adipocytes. The obtained adipocytes were oil red O-stained to measure the lipid content. ADSCs were used as control. The results are shown in FIGS. 42 and 43. ADMPCs were found to be capable of differentiating into adipocytes, that is to say, to have functions as adipose progenitor cells. In addition, the efficiency of such differentiation was high compared to ADSCs. From the above it was verified that ADMPCs were cells that have the capability of differentiating into multipotent cells.

5. Differentiation Capability into Bone Tissue

Figure 44:
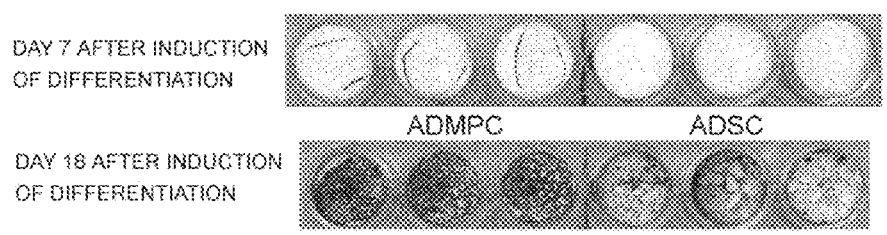
FIG. 44 is a figure comparing the states of differentiation into bones for ADMPC and ADSC by alizarin red staining.
Figure 45:
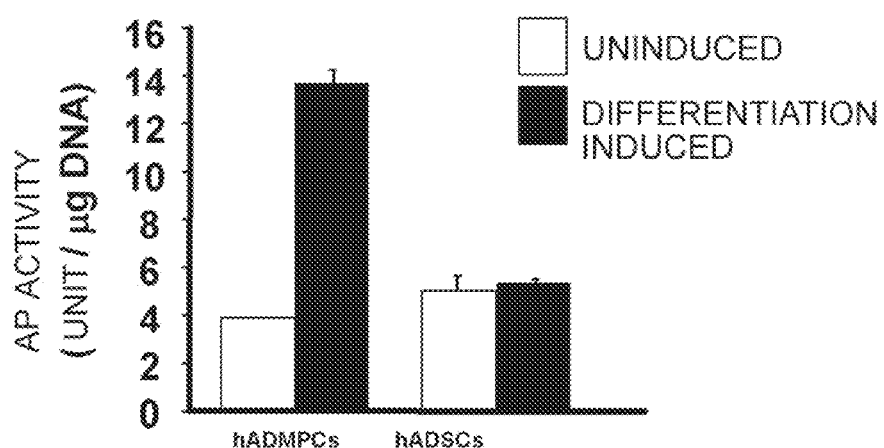
FIG. 45 is a figure comparing the states of differentiation into bones for ADMPC and ADSC by alkaline phosphatase activity.

ADMPCs were cultured for seven days in DMEM containing 10 nM dexamethasone, 50 mg/dl ascorbic acid 2-phosphate, 10 mM β-glycerophosphate (Sigma), and 10% FBS to induce differentiation into bone tissue. The differentiation state was verified by alizarin red staining and alkaline phosphatase (ALPase) activity. Regarding alizarin red staining, the obtained cells were washed three times and fixed with anhydrous ethanol. After fixation, the cells were stained with 1% alizarin red S in 0.1% $NH_4OH$ (pH 6.5) for 5 minutes and washed with $H_2O$. Regarding ALPase activity, well known methods were followed (Bessey, O. A. et al., J. Biol. Chem. 164, 321-329 (1946)). Describing in detail, cells were washed three times, then, homogenized at 0 to 4° C. in 1 ml of 0.9% NaCl and 0.2% Triton X-100 using a glass homogenizer, and centrifuged at 1200 g for 15 minutes. The ALPase activity of the supernatant solution was checked using p-nitrophenyl phosphoric acid (p-NP) as substrate. Specifically, this supernatant solution was assayed in a 0.5M Tris/HCl buffer solution (pH 9.0) containing 0.5 mM pNP and 0.5 mM $MgCl_2$. The reaction mixture was incubated at 37° C. for 30 minutes and the reaction was stopped by the addition of 0.25 volume of 1N NaOH. The hydrolysis of pNP was monitored as the change in the value of the absorbance at 410 nm of the spectrophotometer. p-nitrophenol was used as a standard. One activity unit was defined as the amount that hydrolyzes 1 nmol of p-NP in 1 minute. The ALPase activity per cell was calculated based on the DNA amount. The DNA content was measured by an improvement of a generic method (Labarca, C. et al., Biochem. 102, 344-352 (1980)). After washing, the cells were homogenized at 0 to 4° C. in 1 ml of 2M NaCl/25 mM Tris-HCl (pH 7.4). After centrifugation at 12000 g for 10 minutes, 25 ml of 5 mg/ml bis-benzimidazole was added to 100 ml of supernatant solution. With a spectrofluorometer, excitation was set to 356 nm, and the fluorescence spectrum at 458 nm light emission was monitored. DNA concentration was checked using a standard curve constructed from various concentrations of DNA from calf thymus gland. The results are shown in FIGS. 44 and 45. In comparison to ADSC using conventional method, the ADMPCs according to the present invention showed strong positivity in alizarin red staining and AP activity, verifying that they were easily induced to differentiate into bone tissue. From the above, ADMPCs were shown to have the capabilities to differentiate into tissues cells from multiple lineages including from the pancreas, the liver, the heart, fat, bone and the like.

EXAMPLE 4

Isolation and Culture of Adipose Tissue-Derived Cell

Figure 46:
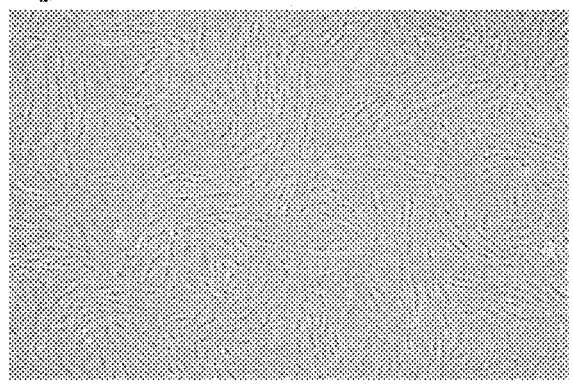
FIG. 46 is a micrograph of the obtained adipose tissue-derived cells.

A human adipose tissue was sliced into 2 to 3 $mm^2$-large fragments and digested using collagenase I. The digestate was cultured for 24 to 36 hours in DMEM containing 10% FBS and antibiotics and treated with 0.02% EDTA to obtain adipose tissue-derived cells. The obtained adipose tissue-derived cells were amplified by 3 to 5 passage cultures in a culture medium containing 60% DMEM (low glucose), 40% MCDB201, 1×ITS (10.0 mg/L insulin, 5.5 mg/L transferrin, 6.7 ng sodium selenite), 10 ng/mL rhEGF, 1 nM dexamethasone, 0.1 mM ascorbic acid and 5% FCS (Hyclone), in a fibronectin-coated dish. A micrograph of adipose tissue-derived cells is shown in FIG. 46.

Acquisition of Undifferentiated Cell from Adipose Tissue-Derived Cells

Figure 47:
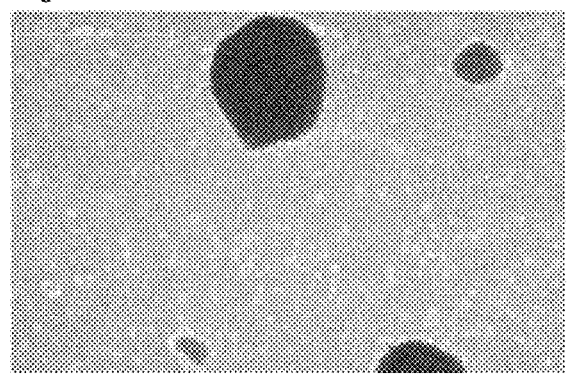
FIG. 47 is a micrograph of the obtained adipospheres.

Cells that were singularized by treating adipose tissue-derived cells treated with 0.25% trypsin/EDTA (Nacalai Tesque) to be dissociated were cultured for 2 to 3 days in knock out DMEM (GIBCO Invitrogen) containing 20% FCS, 1 mM glutamine (GIBCO Invitrogen) and 1% non-essential amino acids (GIBCO Invitrogen), in a low binding culture dish (Hydrocell; CellSeed). The cells autoagglutinated to form adipospheres. A micrograph of adipospheres is shown in FIG. 47.

Formation of Hepatic Lobule-Like Cell Cluster from Undifferentiated Cell

Figure 48:
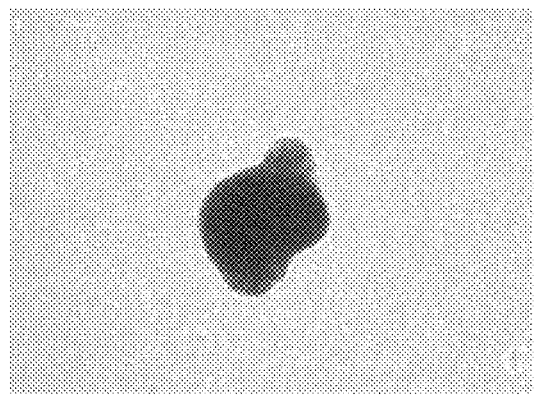
FIG. 48 is a micrograph of the obtained hepatic lobule-like cell cluster.
Figure 49:
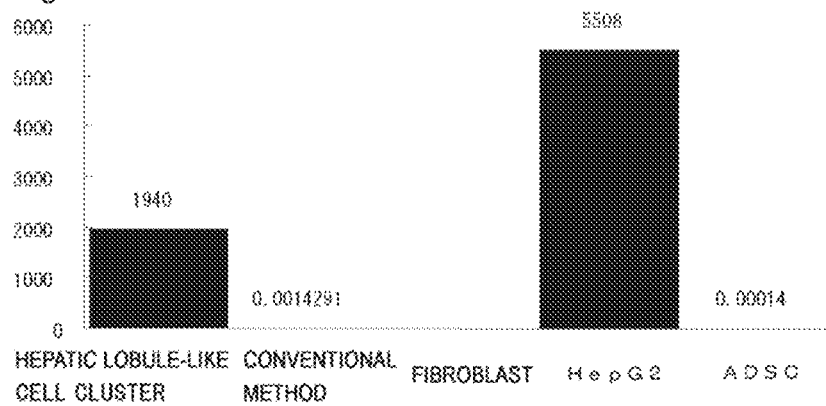
FIG. 49 is a graph showing the results of quantitative RT-PCR for α-fetoprotein. The vertical axis represents the ratio of the expression of α-fetoprotein with respect to the expression of GAPDH.
Figure 50:
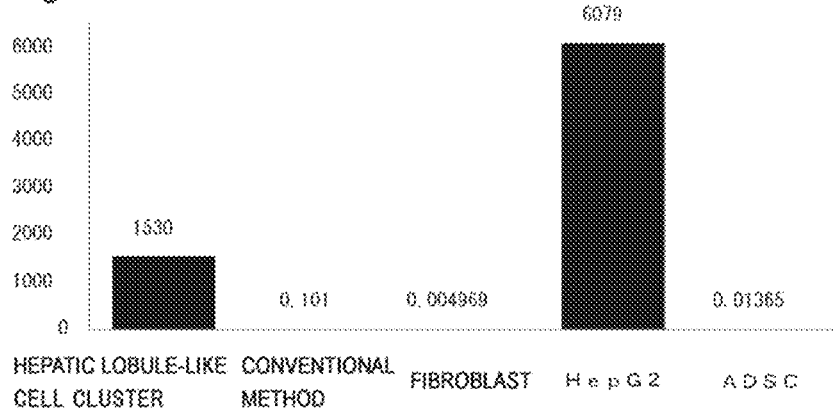
FIG. 50 is a graph showing the results of quantitative RT-PCR for albumin. The vertical axis represents the ratio of the expression of albumin with respect to the expression of GAPDH.
Figure 54:
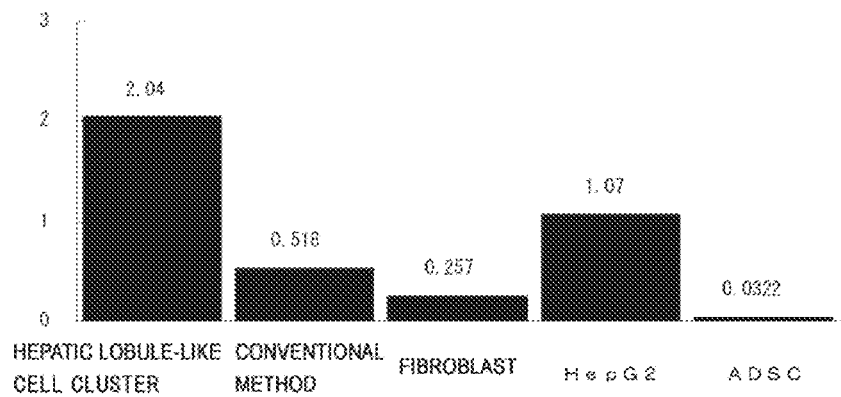
FIG. 54 is a graph showing the results of quantitative RT-PCR for glutamine synthase. The vertical axis represents the ratio of the expression of glutamine synthase with respect to the expression of GAPDH.

The obtained adiposphere was washed 2 to 3 times in PBS (centrifugation at 1000 to 1200 rpm) and cultured for 3 to 4 weeks in a culture medium containing 60% DMEM (low glucose), 40% MCDB201, 1×ITS, 1 nM dexamethasone, 100 μM ascorbic acid, 10 ng/mL rhEGF, bFGF, HGF and OSM (oncostatin M), in a low binding culture dish (Hydrocell; CellSeed). From day 10 of the beginning of the culture, 0.1% DMSO was added to obtain a hepatic lobule-like cell cluster. A micrograph of the obtained hepatic lobule-like cell cluster is shown in FIG. 48.

EXAMPLE 5

Hepatocyte Gene Expression Characteristics of Hepatic Lobule-Like Cell Cluster
1. Extraction of RNA Extraction of RNA from the hepatic lobule-like cell cluster was carried out using RNeasy Protect Mini Kit (QIAGEN), as follows. The hepatic lobule-like cell cluster was recovered, and the buffer RLT containing 10 μl/ml 2-mercaptoethanol (Naacalai Tesqu[13]) was added at a proportion of 600 μl/10$^7$ cell. Cells were homogenized by pipetting with a 20 G needle and then 600 μl of 70% ethanol was added. Transferred onto an RNeay[14] Mini column inside a 2 ml collection tube were 700 μl of the obtained mixed solution, which was centrifuged at 1000 rpm for 15 seconds. Next, 350 μl of buffer RW1 was added onto the column and centrifuged at 1000 rpm for 15 seconds. Added to 70 μl of buffer RDD were 10 μl of DNase I stock solution (QIAGEN), which were tumble-mixed, added to the RNeasy silica gel membrane inside the RNeasy Mini column, and incubated at room temperature for 15 minutes. Added was 350 μl of buffer RW1, and centrifugation was performed at 1000 rpm for 15 seconds. The 2 ml collection tube was replaced with a new one. Added onto the column was 500 μl of buffer RPE, and centrifugation was performed at 1000 rpm for 15 seconds. Further, 500 μl of buffer RPE was added, centrifugation was performed at 1000 rpm for 2 minutes, and then, centrifugation was performed at 1500 rpm for one minute. The column was transferred to a 1.5 ml collection tube, 30 to 50 μl of RNase free water was added to the RNeasy silica gel membrane, and centrifugation was performed at 1000 rpm for one minute to extract RNA.

2. Preparation of Single-Stranded cDNA

To 11.5 μl of the extracted RNA solution, 0.5 μl of 0.5 mM Random Primer (Invitorogen[15]) and 1 μl of 10 mM dNTPmix (Invitorogen[16]) were added, reacted at 65° C. for 5 minutes, and then cooled on ice. To the obtained mixture, 4 μl of 5× First-Strand buffer (Invitorogen[17]), 1 μl of 0.1M DTT (Invitorogen[18]), 1 μl of RNaseOUT (Invitorogen[19]), and 1 μl of SuperScript III RT (Invitorogen[20]) were added, reacted at 25° C. for 5 minutes, at 50° C. for 60 minutes and at 70° C. for 15 minutes to prepare a single-stranded cDNA. The obtained cDNA was stored at 4° C. until use.

3. Real-Time PCR

To 9 μl of the cDNA prepared, 10 μl of TaqMan Universal PCR Master Mix (Applied Biosystems) and 1 μl of TaqMan Gene Expression Assays (Applied Biosystems) were added. Real-time PCR was carried out with Applied Byosytems[21] 7900 Fast Real-Time PCR system, with the following conditions: denaturation at 95° C. for 10 minutes, 40 cycles of 15 seconds at 95° C. and 1 minute at 60° C. The TaqMan probes sued for α-fetoprotein, albumin, CYP1B1, CYP2B6, glutamine synthase, keratin 18 and keratin 19 are shown in Table 3 below. In addition, GAPDH (Applied Biosystems) was used as an internal standard. Hepatocytes obtained by the methods described in Seo M J. et al., 2005 Mar. 4; 328 (1):258-64 (indicated by "conventional methods"), fibroblasts, HepG2, and adipose tissue-derived cells (represented by "ADSC") were used as control samples. The results are shown in FIGS. 49 to 54 (the vertical axes in the figures represent fluorescence intensities). In comparison to the hepatocytes obtained by conventional methods, the hepatic lobule-like cell cluster obtained by methods of the present invention was found to express α-fetoprotein, albumin, keratin 18, keratin 18, keratin 19, CYP1B1 and glutamine synthase highly. In addition, the expression of these genes excepting albumin was significantly higher than that in HepG2.

TABLE 3

| Gene name | Reference sequence | Assay ID |
| --- | --- | --- |
| α-fetoproteinx | NM_001134 | Hs00173490_m1 |
| Albumin | NM_000477 | Hs00609411_m1 |
| Cytochrome P450, family 1, Subfamily B, polypeptide 1 (CYP1B1) | NM_000104 | Hs00164383_m1 |
| Cytochrome P450, family 2, subfamily B, polypeptide 6 | NM_000767 | Hs00167937_g1 |
| Glutamine synthase | NM_002065 | Hs00374213_m1 |
| Keratin 18 | NM_199187/NM_000224 | Hs01941416_g1 |
| Keratin 19 | NM_002276 | Hs00761767_s1 |

EXAMPLE 6

Production of Hepatic Protein by Hepatic Lobule-Like Cell Cluster
A. Western Blot Analysis
1. Sample Preparation Hepatic lobule-like cell cluster was washed three times with PBS (Nacalai Tesque), and then M-PER (PIERCE) was added. Cells were lysed by ultrasonication, centrifuged at 14000 g for 15 minutes to eliminate insoluble cell constituents. Sample buffer (Nacalai Tesque) was added in the same amounts as the sample, boiled at 100° C. for 5 minutes and ice-cooled. The protein concentration in the obtained sample was measured using BCA Protein Assay Reagent (PIERCE).

2. SDS-PAGE

Gel mini plate for electrophoresis (PAG mini "Daiichi"; Daiichi Pure Chemicals Co.) and running buffer were used to perform SDS-PAGE. The amount of protein used was 5 μg. The electrophoresis conditions were 10 mA in the stacking gel and 40 mA in the running gel.

3. Western Blot

The electrophoresed gel above was washed in blotting buffer for 10 minutes. Next, the proteins in the gel were copied onto a nitrocellulose membrane by wet blotting (100 mA, overnight).

4. Immunostaining

Figure 55:
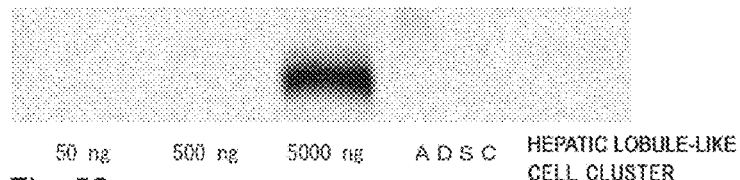
FIG. 55 is the result of western blot analysis for the α-fetoprotein produced by the hepatic lobule-like cell cluster.
Figure 56:
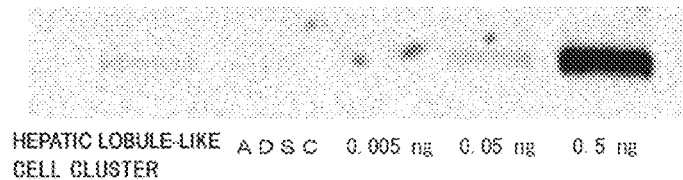
FIG. 56 is the result of western blot analysis for albumin produced by the hepatic lobule-like cell cluster.

The membrane was washed for 10 minutes in PBS containing 0.1% Tween20. Blocking One (Nacalai Tesque) was used and reacted at room temperature for one hour. Reaction was performed for one hour with a 500-fold diluted solution of Human Albumin antibody (BETHYL) or Alpha Fetoprotein Ab-2 (LAB Vision) as primary antibody. Washing was performed for 15 minutes in PBS containing 0.1% Tween20 (three times). Reaction was performed for one hour with a 1000-fold diluted solution of polyclonal pig anti-rabbit immunoglobulin/HRP or polyclonal rabbit anti-goat immunoglobulin/HRP as secondary antibody. Washing was performed for 15 minutes in PBS containing 0.1% Tween20 (three times). The bands were detected using ECL Plus Western Blotting Detection Reagents. The results are shown in FIGS. 55 and 56. The hepatic lobule-like cell cluster obtained by methods of the present invention was found to produce sufficient amounts of α-fetoprotein and albumin.

B. Immunohistochemical Staining

1. Preparation of Sections

The hepatic lobule-like cell cluster was washed three times was PBS (Nacali[22] Tesque) and centrifuged. The obtained pellet was embedded in Tissue-Tek OCT-compound (Sakura Finetech Inc.) and conserved at −30° C. Using a cryostat, 7 μm sections were prepared, pasted on glass and conserved at −30° C.

2. Immunohistochemical Staining

Figure 57:
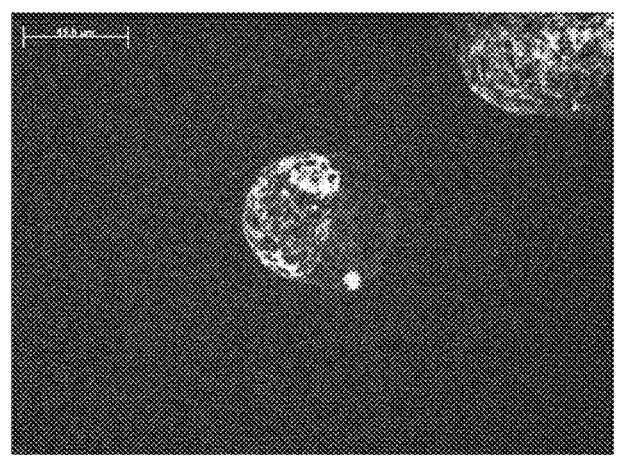
FIG. 57 is a micrograph by immunohistochemical staining showing the presence of α-fetoprotein in a hepatic lobule-like cell cluster.
Figure 58:
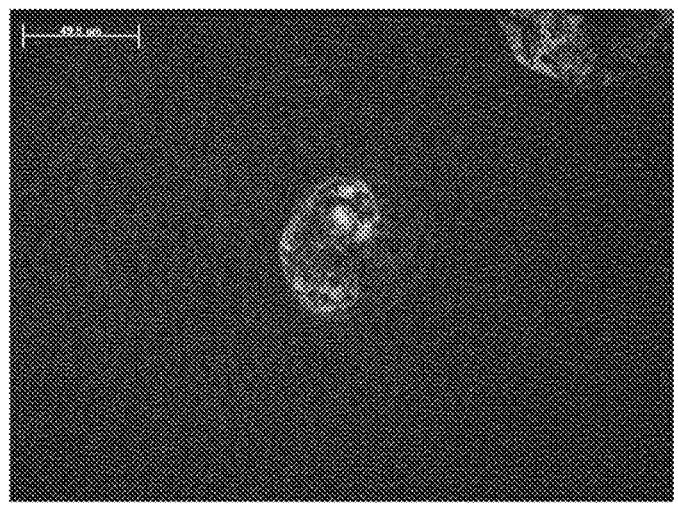
FIG. 58 is a micrograph by immunohistochemical staining showing the presence of albumin in a hepatic lobule-like cell cluster.

The sections described above were dried with a drier and fixed in 4% paraformaldehyde for 30 minutes. Washing in PBS for 5 minutes was performed three times. Blocking One (Nacalai Tesque) was used and reacted at room temperature for one hour. Washing in PBS for 5 minutes was performed three times. Reaction was performed for one hour with a 400-fold diluted solution of the primary antibody polyclonal rabbit anti-human albumin antibody (DAKO) or a 300-fold diluted solution of polyclonal rabbit anti-human α-1-fetoprotein antibody (DAKO). Washing in PBS for 10 minutes was performed three times. Reaction was performed for one hour with 500-fold diluted solution of the secondary antibody AlexaFluor[trademark] 466 goat anti-rabbit IgG antibody (Molecular Probes). Washing in PBS for 10 minutes was performed three times. Embedding was performed using Perma Fluor (Japan Tanner) and observation was carried out with a microscope. The results are shown in FIG. 57 and FIG. 58. The presence of α-fetoprotein, and albumin was verified in hepatic lobule cell population. From this, hepatic lobule cell population was found to produce actually these proteins.

EXAMPLE 7

Incorporation of LDL by Hepatic Lobule-Like Cell Cluster

1. Labeling of LDL with DiI

Human LDL (density: 1.019 to 1.063 g/ml) was isolated. The isolation was carried out from a donor having normal lipoproteins by subjecting the same [23] to ultracentrifugation sequentially, dialysis with saline-EDTA, and then sterilization by filtration with a 0.2 μm filter. Next, the above LDL was incubated with 1,1′-dioctadecyl-3,3,3′,3′-tetramethylindocarbocyanine (DiI; Molecular Probes) (3 mg/ml) in 100 ml of DMSO at 37° C. for 8 hours in 0.5% bovine serum albumin (BSA)/PBS to label the lipoprotein (LDL) with DiI. Thereafter, this lipoprotein was dialyzed with PBS and filtered before use.

2. Incorporation of LDL

Figure 59:
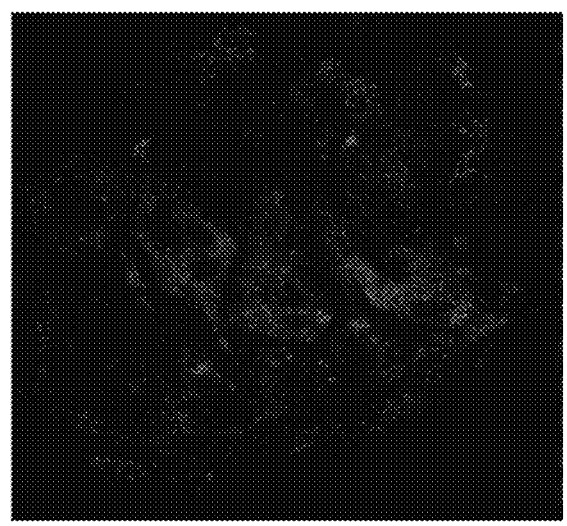
FIG. 59 is a fluorescence micrograph showing the incorporation of DiI-LDL in a hepatic lobule cell population.

In order to examine the incorporation of DiI-LDL, a hepatic lobule cell population, which was differentiated from ADMPC, was incubated in serum-free DMEM containing 10 μg/ml DiI-LDL at 37° C. for 3 hours. Next, the cells were washed three times and mounted over Permaflur [24]. This slide was checked using a confocal laser scanning microscope (Floview FV1000, Olympus). The results are shown in FIG. 59. It is clear from FIG. 59 that DiI-LDL has been incorporated massively in the cytoplasmic regions of the hepatic lobule cell population. From this, it could be confirmed that the hepatic lobule-like cell cluster obtained by the present invention had a function for incorporating LDL.

EXAMPLE 8

Accumulation of Glycogen by Hepatic Lobule-Like Cell Cluster (PAS Staining)

Figure 60:
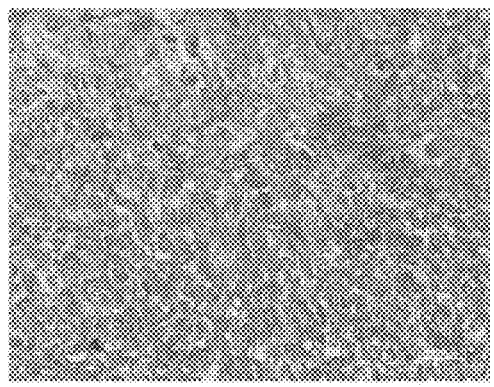
FIG. 60 is a micrograph showing the accumulation of glycogen in a hepatic lobule cell population by PAS staining.

A differentiated hepatic lobule-like cell cluster was fixed with 4% paraformaldehyde and embedded in paraffin. The sample was sliced in a thickness of 5 μm to prepare a section. Thereafter, this section was oxidized with 1% periodic acid for 5 minutes and rinsed three times with deionized water ($dH_2O$). Next, treatment with a Schiff reagent for 15 minutes and rinsing for 5 to 10 minutes with $dH_2O$ were performed. Furthermore, this section was counterstained for 1 minute with Mayer's haematoxylin, rinsed with $dH_2O$ and observed with a light microscope. The results are shown in FIG. 60. From FIG. 60, the presence of many periodic acid Schiff stain (PAS)-positive germ cells could be observed in the hepatic lobule-like cell cluster. From this, the hepatic lobule-like cell cluster obtained by the present invention was shown to have a function for accumulating glycogen.

EXAMPLE 9

Generation of Urea by Hepatic Lobule-Like Cell Cluster

1. Generation of Urea

A hepatic lobule-like cell cluster was incubated for two hours in 5 ml of Hank's balanced salt solution (Gibco) containing 5 mM $NH_4Cl$. The urea concentration in 0.5 ml of supernatant was measured using QuantiChrom Urea Assay Kit (Bioassay Systems). The obtained concentration was multiplied by the total volume of supernatant to calculate the total amount of urea generated. HepG2 was used as control.

2. Measurement of DNA Amount

Hank's balanced salt solution containing $NH_4Cl$ was eliminated and the hepatic lobule-like cell cluster was washed in PBS. A buffer solution was added, and ultrasonication was performed to homogenize the cells. To 50 μl of cell homogenate, 1 ml of buffer solution was added, 50 μl of coloring solution was further added, and stirring was performed. The fluorescence value of the obtained solution was measured at 356 nm excitation and 458 nm emission to determined the DNA concentration. To calculate the overall DNA, the DNA concentration was multiplied by the volume of buffer solution added.

3. Amount of Urea Generated

Figure 61:
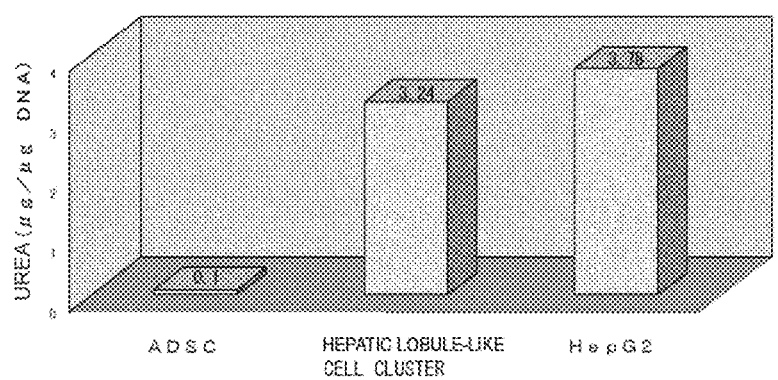
FIG. 61 is a graph showing the amount of urea generated by a hepatic lobule-like cell cluster.

The obtained total amount of urea generated was divided by the overall DNA amount to calculate the overall amount of urea generated. The results are shown in FIG. 61. The hepatic lobule-like cell cluster was found to generate a sufficient amount of urea compared to HepG2. From this, it could be confirmed that the hepatic lobule-like cell cluster obtained by the present invention had sufficient detoxification action.

EXAMPLE 10

Grafting Effect of Hepatic Lobule-Like Cell Cluster in Mouse Hepatitis Model

1. Preparation of Mouse Hepatitis Model

A mouse hepatitis model was prepared by intraperitoneal injection into NOD-SCID mouse of carbon tetrachloride ($CCl_4$) at 300 μl/kg, twice weekly and for 12 weeks.

2. Grafting of Hepatic Lobule-Like Cell Cluster

A hepatic lobule-like cell cluster was washed with Hank's balanced salt solution, centrifuged and pelleted. The above mouse was anaesthetized with sevofluene[25]. A celiotomy [26] was performed by left paramedian incision, the left kidney was exposed, the renal capsule[27] separated to create a pocket. The pelletized cell population was injected and grafted inside the created pocket. The abdominal wall was closed in two layers.

3. Analyses

Figure 62:
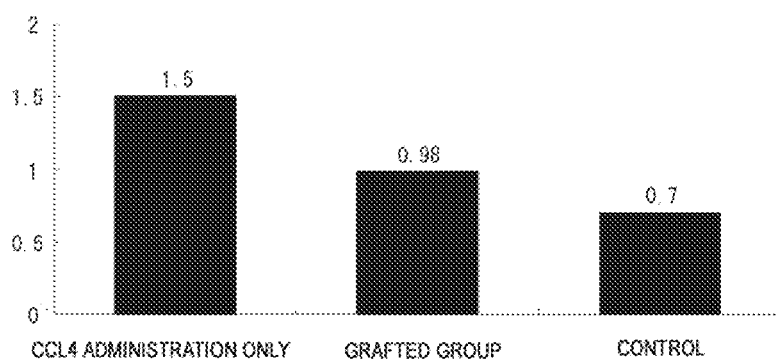
FIG. 62 is a graph showing the effects from the grafting of a hepatic lobule-like cell cluster in a hepatitis mouse model. The vertical axis represents total bilirubin concentration (mg/dL).
Figure 63:
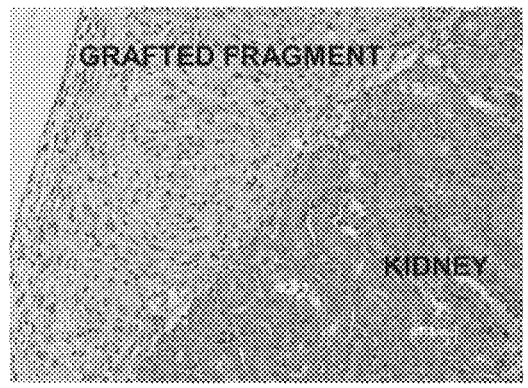
FIG. 63 micrograph by HE staining showing a survival of hepatic lobule-like cell cluster after grafting of the hepatic lobule-like cell cluster under the renal capsule[2] of mouse.
Figure 64:
FIG. 64 is a micrograph by immunohistological staining showing the expression of albumin in a hepatic lobule-like cell cluster after grafting.
Figure 65:
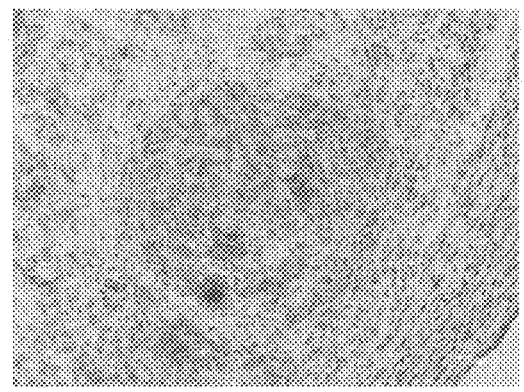
FIG. 65 is a micrograph by PAS staining showing the accumulation of glycogen in a hepatic lobule-like cell cluster after grafting.

On day 10 of grafting blood was collected from the mice to measure blood concentration of bilirubin. The results are shown in FIG. 62. The blood concentration of bilirubin was found to decreased in the group grafted with the hepatic lobule-like cell cluster compared to the group with no grafting performed. In addition, the following histological analysis was performed using the above left kidney. The left kidney grafted with the hepatic lobule-like cell cluster was taken out and fixed immediately with 10% formalin. Next, embedding with paraffin was performed, haematoxylin and eosin staining (FIG. 63) and PAS staining (FIG. 65) were performed by similar methods to above. On one hand, kidney grafted with hepatic lobule-like cell cluster was also used to perform immunofluorescence staining for albumin. First, the tissue was placed in OCT-compound (Sakura Fineteck Inc.) and frozen immediately. A 7 μm section was prepared and fixed in 4% paraformaldehyde/PBS (WAKO) for 30 minutes. This fixed section was incubated with a blocking solution (Blocking One; Nacalai Tesque). Next, incubation with anti-human ALB antibody (adsorbed with goat polyclonal, cow, mouse and pig ALB and affinity-purified; Bethyl Laboratories), followed by AlexaFluor 546 donkey anti-goat IgG antibody (Molecular Probes), was performed. The treated section was observed with a fluorescence microscope (BX61, Olympus) (FIG. 64). Grafting of hepatic lobule-like cell cluster could be confirmed from FIG. 63. ALB antibody and PAS staining-positive germ cells could be observed from each of FIG. 64 and FIG. 65, revealing that albumin was expressed and that glycogen has accumulated. These indicate that the liver function is maintained. From the above, the hepatic lobule-like cell cluster that can be obtained by the methods of the present invention was found to be effective in treating a disease that occurs due to a decrease in liver function.

INDUSTRIAL APPLICABILITY

Since the present invention allows a cell population containing an adipose tissue-derived multipotent progenitor cell, a method for obtaining an adipose tissue-derived multipotent progenitor cell from an adipose tissue and an adipose tissue-derived multipotent progenitor cell that can be obtained thereby to be obtained, it is usable in regenerative medical therapy and the research field thereof.

SEQUENCE LISTING FREE TEXT

SEQ ID NO: 1: Islet-1 forward primer
SEQ ID NO: 2: Islet-1 reverse primer
SEQ ID NO: 3: Nkx2.5 forward primer
SEQ ID NO: 4: Nkx2.5 reverse primer
SEQ ID NO: 5: GATA-4 forward primer
SEQ ID NO: 6: GATA-4 reverse primer
SEQ ID NO: 7: α-CA forward primer
SEQ ID NO: 8: α-CA reverse primer
SEQ ID NO: 9: MLC2v forward primer
SEQ ID NO: 10: MLC2v reverse primer
SEQ ID NO: 11: MHC forward primer
SEQ ID NO: 12: MHC reverse primer
SEQ ID NO: 13: GAPDH forward primer
SEQ ID NO: 14: GAPDH reverse primer
SEQ ID NO: 15: nestin forward primer
SEQ ID NO: 16: nestin reverse primer
SEQ ID NO: 17: Neurofilament 68 forward primer
SEQ ID NO: 18: Neurofilament 68 reverse primer
SEQ ID NO: 19: somatostatin forward primer
SEQ ID NO: 20: somatostatin reverse primer
SEQ ID NO: 21: snail forward primer
SEQ ID NO: 22: snail reverse primer
SEQ ID NO: 23: slug forward primer
SEQ ID NO: 24: slug reverse primer

The invention claimed is:

1. A method for increasing purity of Islet-1 expressing adipose tissue-derived multipotent progenitor cell in a culture medium from an adipose tissue, comprising:
(a) slicing and digesting adipose tissue to make an adipose cell extract of separated cells of adipose tissue-derived cell population;
(b) clarifying the separated cells from naturally occurring tissue and digestion products by centrifugation;
(c) selectively removing erythrocytes from the clarified adipose tissue-derived cell population by the density method;
(d) culturing in the presence of feeder cells and then washing the erythrocyte-free clarified adipose tissue-derived cell population; and
(e) selectively removing vascular endothelial cells from the cultured and washed erythrocyte-free clarified adipose tissue-derived cell population by treatment with EDTA
thereby forming a tissue culture enriched in Islet-1 expressing adipose tissue-derived multipotent progenitor cell population with respect to erythrocytes and respect to vascular endothelial cells, and having a low fibroblast contamination comprising a 23 percent fibroblast cell contamination.

2. The method according to claim 1, further comprising culturing the culture of Islet-1 expressing adipose tissue-derived multipotent progenitor cell in suspension medium to produce a hepatic lobule-like cell cluster.

3. The method according to claim 2, wherein culturing the culture of Islet-1 expressing adipose tissue-derived multipotent progenitor cell in suspension medium comprises culturing for 3 to 4 weeks in 60% DMEM (low glucose), rhEGF, bFGF, HGF and OSM.

4. The method according to claim 3, further comprising a step of adding DMSO to the suspension culture medium.

5. The method according to claim 2, wherein the hepatic lobule-like cluster comprises at least one hepatocyte.

6. The method according to claim 5, further comprising a step of adding DMSO to the suspension culture medium.

7. The method according to claim 1, wherein the prepared culture lacks erythrocyte cells and vascular endothelial cells and contains feeder cells.

* * * * *